(12) United States Patent
Bombard et al.

(10) Patent No.: US 6,398,797 B2
(45) Date of Patent: Jun. 4, 2002

(54) TISSUE BONDING SYSTEM AND METHOD FOR CONTROLLING A TISSUE SITE DURING ANASTOMOSIS

(75) Inventors: David Bombard; Theodore Bender, both of San Francisco; Tenny Chang, Mountain View; Jaime Vargas, Palo Alto; Michael Hendricksen, Redwood City; Stephen A. Yencho, Menlo Park; Jamey Nielsen, San Francisco; Bernard A. Hausen, Menlo Park; Brendan Donohoe, San Francisco, all of CA (US)

(73) Assignee: Cardica, Inc., Menlo Park, CA (US)

( * ) Notice: Subject to any disclaimer, the term of this patent is extended or adjusted under 35 U.S.C. 154(b) by 0 days.

(21) Appl. No.: 09/725,232

(22) Filed: Nov. 29, 2000

Related U.S. Application Data

(63) Continuation-in-part of application No. 09/363,255, filed on Jul. 28, 1999.

(51) Int. Cl.[7] .............................................. A61B 17/04
(52) U.S. Cl. ................... 606/153; 227/175.1; 227/176.1
(58) Field of Search ....................... 606/153; 227/175.1, 227/176.1

(56) References Cited

U.S. PATENT DOCUMENTS

| | | | |
|---|---|---|---|
| 3,254,650 A | 6/1966 | Collito | |
| 3,774,615 A | 11/1973 | Lim et al. | 128/334 |
| 4,350,160 A | 9/1982 | Kolesov et al. | 128/334 |
| 4,352,358 A | 10/1982 | Angelchik | 128/334 |
| 4,368,736 A | 1/1983 | Kaster | 128/334 |
| 4,523,592 A | 6/1985 | Daniel | 128/334 |
| 4,553,542 A | 11/1985 | Schenck et al. | 128/334 |
| 4,593,693 A | 6/1986 | Schenck | 128/334 |
| 4,607,637 A | 8/1986 | Berggren et al. | 128/334 |
| 4,624,255 A | 11/1986 | Schenck et al. | 128/334 |
| 4,624,257 A | 11/1986 | Berggren et al. | 128/334 |

(List continued on next page.)

FOREIGN PATENT DOCUMENTS

| | | |
|---|---|---|
| DK | 19732234 | 7/1997 |
| EP | 0938870 | 9/1999 |
| FR | 2316910 | 7/1996 |
| WO | WO9819625 | 5/1998 |
| WO | WO9911178 | 3/1999 |

*Primary Examiner*—Gary Jackson
(74) *Attorney, Agent, or Firm*—Brian A. Schar; Cindy A. Lynch

(57) ABSTRACT

A method and system for performing anastomosis uses an anvil to control and support a tissue site during an anastomosis procedure involving tissue bonding techniques such as tissue welding and adhesive tissue bonding. The anvil is particularly useful for supporting a wall of a coronary artery during attachment of a graft vessel in a coronary artery bypass graft procedure. The anvil is inserted into a pressurized or unpressurized target vessel and is pulled against an inner wall of the target vessel causing tenting of the thin tissue of the vessel wall. A graft vessel is then advanced to the anastomosis site and an end of the graft vessel is positioned adjacent an exterior of the target vessel. When tissue welding is used, a graft vessel fixture is positioned over the tissue surfaces to be welded in order to clamp the graft and target vessel tissue together. The tissue contacting surfaces of the anvil and/or graft vessel fixture are provided with one or more energy applying surfaces. Energy in the form of RF power, laser energy or ultrasonic energy is then applied to the compressed graft and target vessel tissue to weld the vessels together. When adhesive bonding is used, the adhesive may be applied to mating surfaces of the graft and/or target vessels either before or after the vessels are brought into contact. After tissue bonding is complete, an incision is formed in the wall of the target vessel to allow blood flow between the target vessel and the graft vessel. The incision may be made with an electro-cautery cutting device.

43 Claims, 19 Drawing Sheets

U.S. PATENT DOCUMENTS

| | | | |
|---|---|---|---|
| 4,657,019 A | 4/1987 | Walsh et al. | 128/334 |
| 4,747,407 A | 5/1988 | Liu et al. | 128/334 |
| 4,773,420 A | 9/1988 | Green | 227/19 |
| 4,892,098 A | 1/1990 | Sauer | 606/18 |
| 4,907,591 A | 3/1990 | Vasconcellos et al. | 606/154 |
| 4,917,087 A | 4/1990 | Walsh et al. | 606/153 |
| 4,917,090 A | 4/1990 | Berggren et al. | 606/153 |
| 4,917,091 A | 4/1990 | Berggren et al. | 606/153 |
| 4,930,674 A | 6/1990 | Barak | 227/179 |
| 5,119,983 A | 6/1992 | Green et al. | 227/179 |
| 5,156,613 A | 10/1992 | Sawyer | 606/213 |
| 5,234,447 A | 8/1993 | Kaster et al. | 606/153 |
| 5,300,065 A | 4/1994 | Anderson | 606/13 |
| 5,336,233 A | 8/1994 | Chen | 606/153 |
| 5,364,389 A | 11/1994 | Anderson | 606/8 |
| 5,366,462 A | 11/1994 | Kaster et al. | 606/153 |
| 5,395,030 A | 3/1995 | Kuramoto et al. | 227/179 |
| 5,540,677 A | 7/1996 | Sinofsky | 606/8 |
| 5,571,167 A | 11/1996 | Maginot | 623/1 |
| 5,611,794 A | 3/1997 | Sauer et al. | |
| 5,669,918 A | 9/1997 | Balazs et al. | 606/139 |
| 5,669,934 A | 9/1997 | Sawyer | 606/213 |
| 5,676,670 A | 10/1997 | Kim | 606/108 |
| 5,695,504 A | 12/1997 | Gifford, III et al. | 606/153 |
| 5,702,412 A | 12/1997 | Popov et al. | 606/159 |
| 5,707,369 A | 1/1998 | Vaitekunas et al. | 606/31 |
| 5,707,380 A | 1/1998 | Hinchliffe et al. | 606/153 |
| 5,725,544 A | 3/1998 | Rygaard | 606/167 |
| 5,749,895 A | 5/1998 | Sawyer et al. | 606/214 |
| 5,776,130 A | 7/1998 | Buysse et al. | 606/48 |
| 5,797,920 A | 8/1998 | Kim | 606/108 |
| 5,817,113 A | 10/1998 | Gifford, III et al. | 606/153 |
| 5,824,015 A | 10/1998 | Sawyer | 606/214 |
| 5,827,265 A | 10/1998 | Glinsky et al. | 606/8 |
| 5,827,271 A | 10/1998 | Buysse et al. | 606/40 |
| 5,904,697 A | 5/1999 | Gifford, III et al. | 606/155 |
| 6,004,335 A | 12/1999 | Vaitekunas et al. | 606/169 |
| 6,039,733 A | 3/2000 | Buysse et al. | 606/40 |
| 6,248,117 B1 * | 6/2001 | Blatter | 606/153 |

* cited by examiner

TISSUE BONDING SYSTEM AND METHOD FOR CONTROLLING A TISSUE SITE DURING ANASTOMOSIS

This application is a continuation-in-part of U.S. patent application Ser. No. 09/363,255, entitled "Anastomosis System and Method for Controlling a Tissue Site", filed Jul. 28, 1999, which is incorporated herein by reference in its entirety.

BACKGROUND OF THE INVENTION

1. Field of the Related Art

The invention relates to an anastomosis system and method for controlling a tissue site in an anastomosis procedure wherein blood vessels or other tubular or hollow organs are joined together by tissue bonding.

2. Background of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery, such as the aorta. The suturing process is a time consuming and difficult procedure requiring a high level of surgical skill. In order to perform the suturing of the graft to a target vessel such as the coronary artery or the blood supplying artery the surgeon generally has an assistant hold the edges of the incision in the target vessel while the surgeon takes small stitches as close as possible to the edges of the incision. This suturing requires a high degree of precision and is quite time consuming. In addition, during conventional CABG procedures blood flow at the anastomosis site is stopped during suturing. This prevents bleeding from the incision site but also prevents blood from reaching a portion of the heart muscle served by the vessel.

Various alternatives to suturing are known for performing anastomosis. These techniques generally involve securing the tissue with mechanical fasteners such as staples or fittings which compress the tissue surfaces together. Sutureless techniques for performing anastomosis are disclosed in U.S. Pat. Nos. 3,254,650; 3,774,615; 4,350,160; 4,352,358; 4,368,736; 4,523,592; 4,553,542; 4,593,693; 4,607,637; 4,624,255; 4,624,257; 4,657,019; 4,747,407; 4,907,591; 4,917,087; 4,917,090; 4,917,091; 5,119,983; 5,234,447; 5,336,233; 5,366,462; 5,456,714; 5,571,167; 5,669,918; 5,676,670; 5,695,504; 5,702,412; 5,707,380; 5,725,544; 5,797,920; 5,817,113; and 5,904,697.

While offering certain advantages over suturing, mechanical fastening techniques such as stapling still have disadvantages. Staples, for example, can produce high mechanical loads which may result in tearing of the tissue around the staples. As a result, staples cannot be placed too close to the incision cite in the target vessel.

Another alternative to suturing in general surgical procedures is tissue bonding. Tissue bonding methods include adhesive bonding and tissue welding. Adhesive bonding generally involves applying a tissue adhesive to either or both of the tissue mating surfaces and applying clamping pressure until the adhesive sets. Tissue welding is generally accomplished by heating the tissue through energy dissipation in the affected tissue. The energy applied to the tissue can be in the form of electrical power (usually RF power), light energy (e.g., laser) or ultrasonic energy. During welding, the heated tissue in the weld region undergoes cellular dehydration and denaturation of proteins which results in formation of the weld. Tissue bonding procedures are disclosed in U.S. Pat. Nos. 4,892,098 5,156,613; 5,290,278; 5,300,065; 5,364,389; 5,540,677; 5,611,794; 5,669,934; 5,707,369; 5,749,895; 5,824,015; 5,827,265; and 6,004,335.

Tissue bonding techniques, however, have met with limited success when used for performing vascular anastomosis. With tissue welding, achieving a strong bond requires not only precise control of energy delivery to the tissue in the weld region but also proper tissue apposition. Energy delivery is important to ensure that the desired amount of energy is absorbed by the tissue. Tissue apposition is important because the sections of tissue to be welded together must be in substantial abutment and accurate alignment to ensure that the energy applied to the tissue effectively fuses the tissue in the weld area. Deficient apposition can cause leakage or the formation of weak bonds. Tissue apposition is also important for adhesive bonding where the tissue mating surfaces must be held in proper position until the adhesive sets. Proper tissue apposition during vascular anastomosis is particularly difficult to achieve due to the small size and the flexible, circular configuration of the blood vessels involved.

Accordingly, there exists a need to provide a device for performing vascular anastomosis by tissue bonding. There also exists a need for a device which provides precise apposition of the graft and target vessels for tissue bonding during in an end-to-side anastomosis procedure.

SUMMARY OF THE INVENTION

The present invention relates to a system and method for performing vascular anastomosis by tissue bonding techniques. The present invention also relates to a method of controlling a tissue site during an anastomosis procedure wherein a graft vessel and a target vessel are attached together using a tissue bonding technique. Suitable tissue bonding techniques include adhesive bonding and tissue welding. The anastomosis system and method of the present invention may be used on a pressurized or unpressurized target vessel.

In accordance with one aspect of the present invention, a method of performing anastomosis is provided. The method employs an anastomosis system including an elongated anvil having tissue contacting surfaces and a graft vessel fixture movable with respect to the anvil. The graft vessel fixture further includes clamping members each having one or more clamping surfaces adapted to compress the tissue on opposite sides of the graft vessel against the anvil. The method involves steps of: inserting the elongated anvil through the wall of a target blood vessel and positioning the elongated anvil along an interior of the target blood vessel wall; positioning a graft vessel adjacent an exterior of the target blood vessel wall; moving the fixture toward the anvil to clamp the graft and target vessel tissue between the tissue contacting surfaces of the anvil and the clamping surfaces of the fixture; and applying energy to the tissue clamped between the electrode surfaces on the anvil and the clamping surfaces of the fixture to secure the graft and target vessels together. In a preferred embodiment of the present invention, the method also comprises steps of making an opening in the target vessel to allow blood to flow between the target vessel and the graft vessel and removing the anvil.

In accordance with another aspect of the present invention, an anastomosis system is provided for connecting a graft vessel to a target vessel by the application of energy. The anastomosis system includes an elongated anvil having tissue contacting surfaces and a graft vessel fixture. The fixture includes clamping members each of which has one or more clamping surfaces adapted to compress the graft and target vessel tissue on opposite sides of the graft vessel against the anvil. The fixture is movable relative to the anvil so as to allow the graft and target vessel tissue to be clamped between the anvil and the fixture at the anastomosis site. Furthermore, the tissue contacting surfaces of the anvil and/or the clamping surfaces of the fixture are provided with one or more energy applying surfaces.

In accordance with another aspect of the present invention, an anvil for use in performing anastomosis between a graft vessel and a target vessel is provided. The anvil includes a handle and an elongated anvil arm extending from the handle. The anvil arm has at least one energy applying surface on an upper tissue contacting surface thereof.

In accordance with another aspect of the present invention, a method of performing an anastomosis between a target vessel and the end of a graft vessel is provided. The method includes steps of: applying a tissue adhesive to mating surfaces of the graft vessel and/or target vessel; inserting an elongated anvil through the wall of the target vessel and positioning the anvil along an interior of the target vessel wall; positioning the end of the graft vessel adjacent an exterior of the target vessel wall; and curing the adhesive.

In accordance with a further aspect of the present invention, an anastomosis system for connecting a graft vessel to a target vessel using a tissue adhesive is disclosed. The anastomosis system includes an elongated anvil having tissue contacting surfaces thereon and a graft vessel fixture including clamping members each having one or more clamping surfaces adapted to compress the graft and target vessel tissue on opposite sides of the graft vessel against the tissue contacting surfaces of the anvil. The fixture is movable relative to the anvil so as to allow the graft and target vessel tissue to be clamped between the anvil and the fixture at the anastomosis site. The anvil and/or the graft vessel fixture are provided with one or more tissue adhesive applicators adapted to supply a tissue adhesive to mating surfaces of the graft and/or target vessel.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The anastomosis system and method according to the present invention uses an anvil to control and support a tissue site during an anastomosis procedure wherein the graft and target vessel are attached together using a tissue bonding procedure such as adhesive bonding or tissue welding. The anvil is particularly useful for supporting a wall of a coronary artery during attachment of a graft vessel to the coronary artery in a coronary artery bypass graft procedure. The anvil supports the wall of the coronary artery which is generally very thin, difficult to grasp, and susceptible to tearing. Although the present invention is particularly useful for performing anastomosis on blood vessels and for controlling very thin tissues such as the walls of the coronary arteries, the anvil may also be used for performing anastomosis on other vessels and for controlling other tissue sites.

Figure 1A:
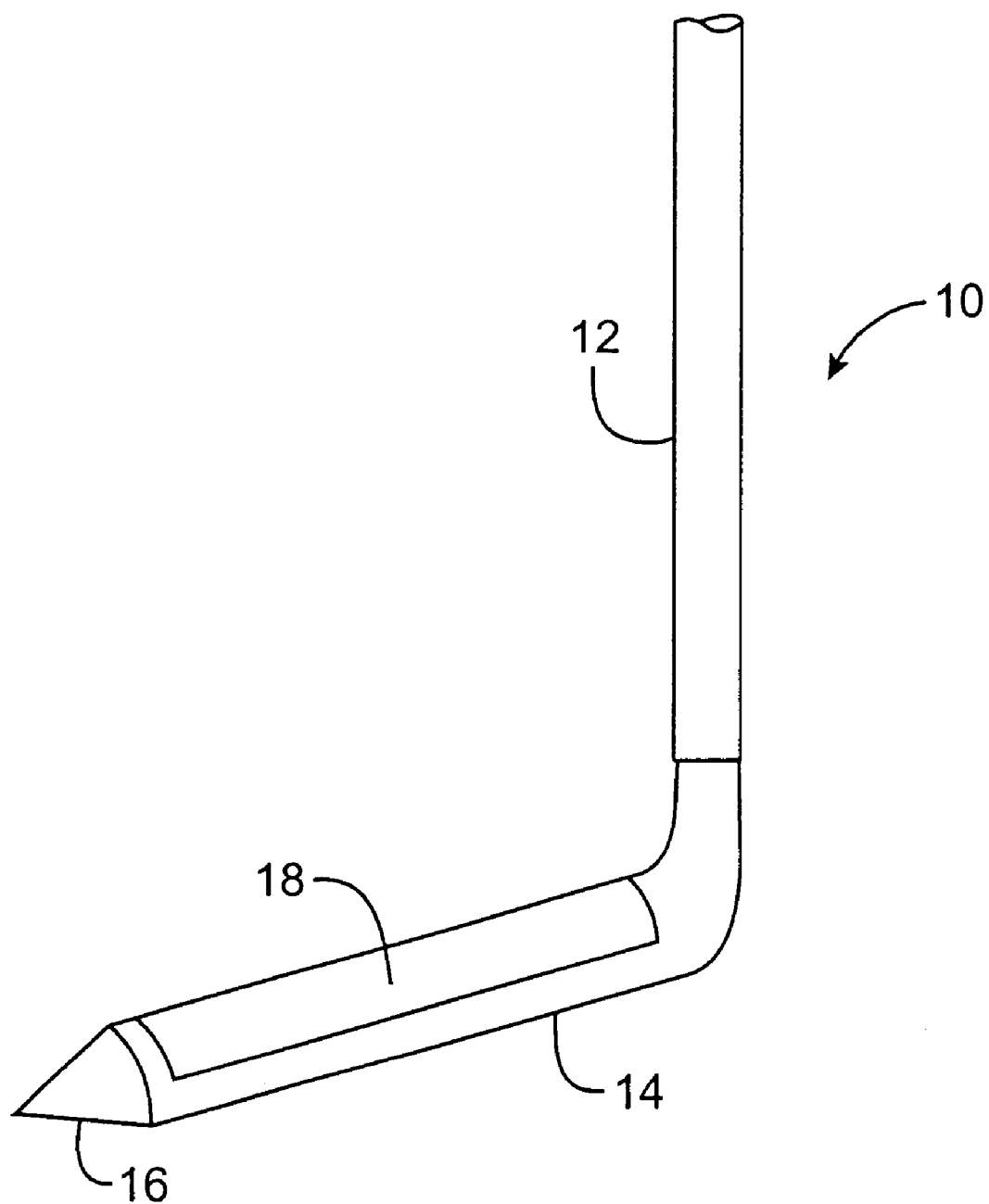
FIG. 1A is a perspective view of a portion of an anvil according to the present invention.

As shown in FIG. 1A, an anvil 10 according to one aspect of the present invention includes a handle 12 and an anvil arm 14 extending substantially perpendicularly from the handle. As shown in FIG. 1A, the anvil arm 14 can have a sharp distal end 16 for puncturing the tissue of a target vessel to insert the anvil arm 14 into the target vessel. In order to apply energy to the tissue at the anastomosis site, the anvil arm 14 can be provided with at least one energy applying surface 18 on an upper tissue contacting surface thereof. Additionally, the anvil arm can be provided with a sensor 11 such as a temperature or impedance sensor.

When tissue bonding is accomplished by RF welding, the tissue contacting surfaces of the anvil arm can be provided with one or more electrodes for applying RF energy to the weld region. The anvil arm itself may function as an electrode or one or more electrically isolated electrode patches may be formed on the tissue contacting surfaces of the anvil arm. For example, the anvil arm may comprise two substantially parallel elongated electrode surfaces on either side of the upper tissue contacting surface of the anvil arm. Further, there may be a plurality of discontinuous electrode patches on either side of the upper tissue contacting surface of the anvil arm each of which is capable of being powered separately. The anvil arm may also have projections, each of which can form an electrode surface capable of being powered separately. By employing a plurality of electrically isolated electrode patches, spot welds can be formed.

Figure 1B:
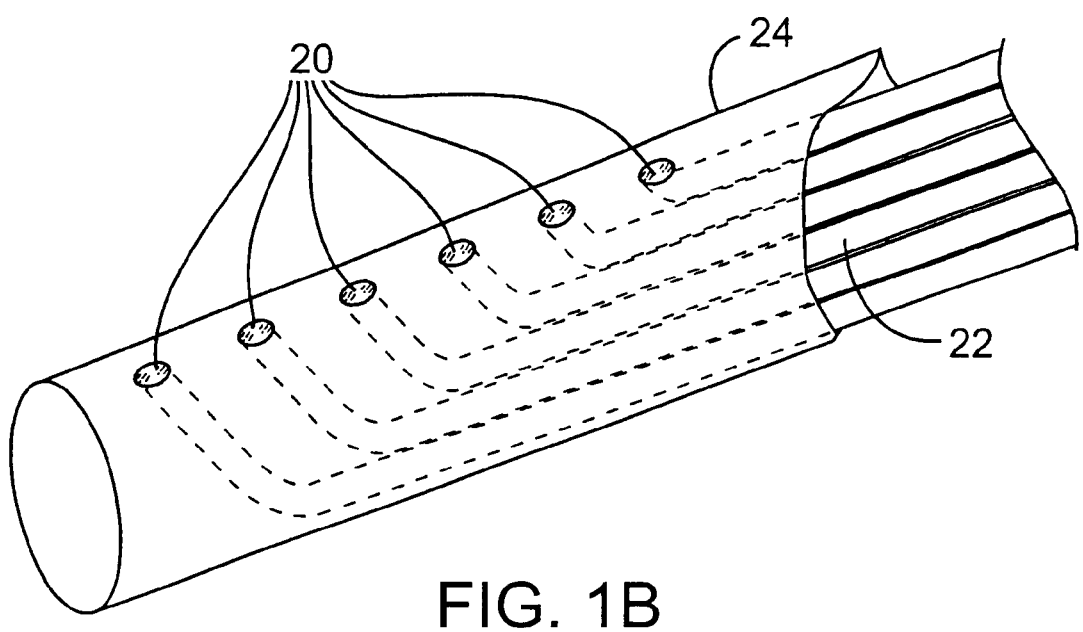
FIG. 1B is a perspective view of a portion of an anvil arm according to the present invention having optical fiber ends exposed at a tissue contacting surface thereof.

When tissue bonding is accomplished with laser welding, the anvil arm can be provided with means for supplying laser energy to tissue in the weld region. In FIG. 1B, an anvil arm 24 is shown having multiple optical fibers ends 20 exposed on the tissue contacting surfaces of the anvil arm for delivery of laser energy to tissue surfaces adjacent the anvil. As shown, the optical fibers 22 can be routed through the inside of the anvil to a light source inside or outside of the anvil.

Figure 1C:
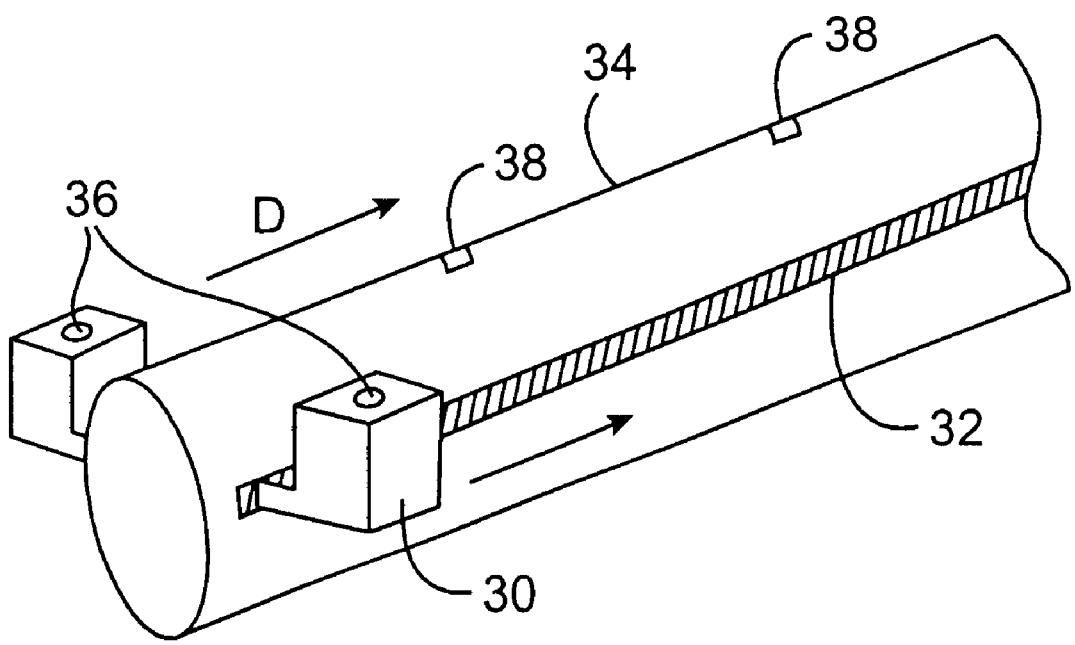
FIG. 1C is a perspective view of a portion of an anvil arm according to the present invention having an optical fiber assembly movably mounted in a track therein.

In FIG. 1C, an alternative embodiment of an anvil arm is shown which has an energy applying assembly 30 movably mounted in a track 32 on each side of the anvil arm 34. The energy applying assembly may include light fibers for application of light energy, electrodes for applying electrical or RF energy or other energy applying members. The track 32 allows the exposed optical fiber ends or electrodes 36 to be moved along the length of the anvil arm in the direction D. By powering the optical fibers or electrodes and moving the energy applying assembly along the length of the anvil, a continuous weld line can be formed on each side of the anvil. Further, the energy may be pulsed to form an intermittent weld line.

In addition to an energy applying surface, the anvil may also be provided with one or more sensors. For example, one or more temperature or impedance sensors 38 may be incorporated into the anvil to accurately measure the temperature of the intimal surface of the target vessel during the tissue welding process. Various temperature measuring devices which could be used for this purpose are known in the art including, but not limited to, thermocouples, thermistors and resistance temperature devices (RTDs). Measurement of the temperature can allow for feedback control of the tissue welding process to prevent overheating and damage to the intimal surfaces of the target vessel. The power supplied to the electrodes can be modulated in response to the output from the sensor.

In the case of RF welding, the sensor may also be an impedance sensor used to monitor the amount of energy being delivered to the tissue thus allowing power to be modulated based on measured values of tissue impedance. Tissue impedance may be measured during application of therapeutic energy or by supplying a small amount of non-therapeutic energy to the electrodes. The anvil may also be provided with a cooling ability to prevent overheating of the tissue of the target vessel. Examples of cooling means suitable for use with the anvil include heat sinks and micro-fluidic cooling channels for the circulation of a heat transfer fluid.

Figure 2A:
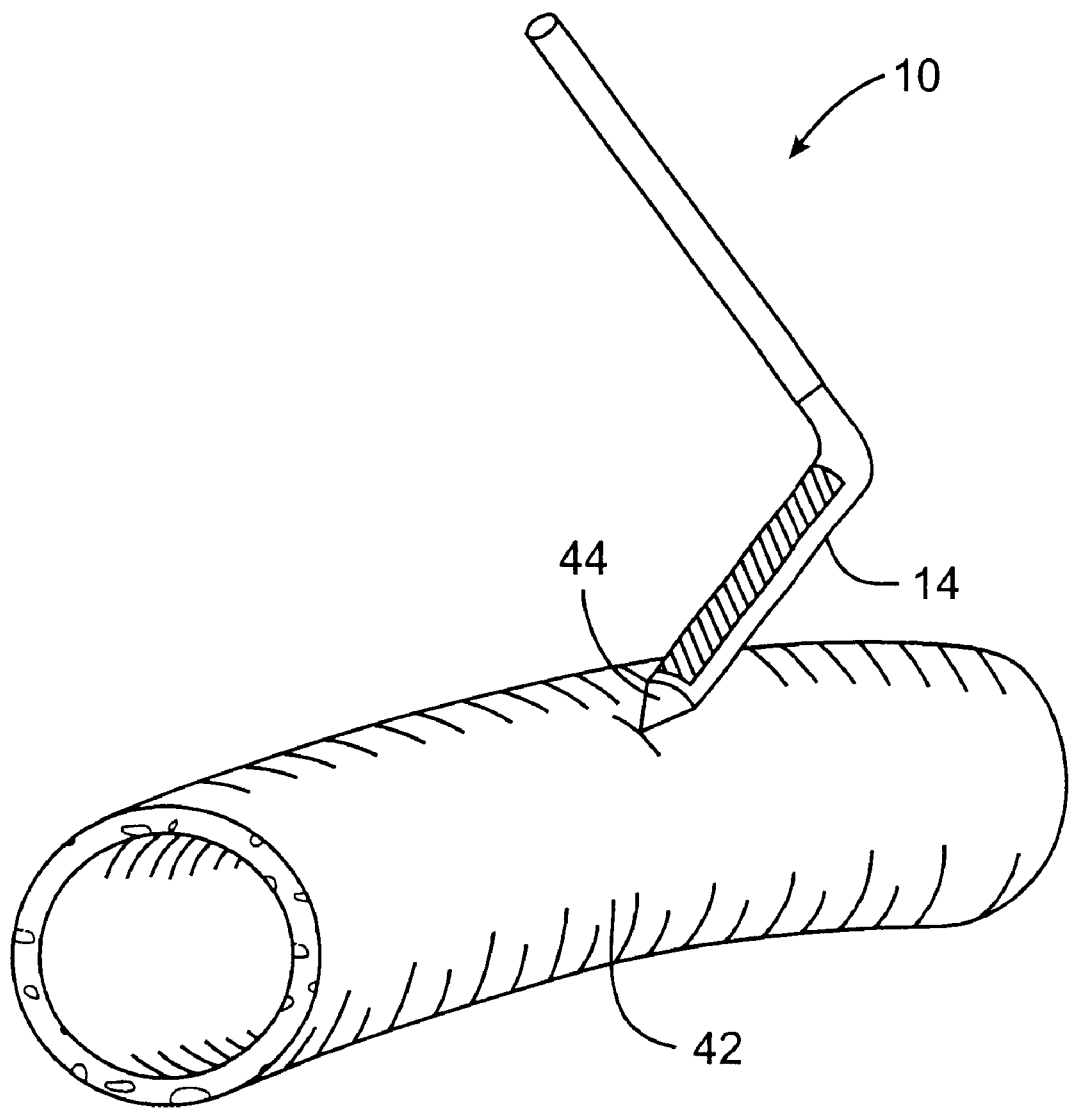
FIG. 2A is a perspective view of the anvil of FIG. 1A being inserted into a target vessel.

As illustrated in FIG. 2A, the anvil arm 14 can be inserted into a pressurized or un-pressurized target vessel 42 by puncturing the target vessel with the sharp distal end 16 of the anvil arm. The hole in the target vessel 42 can also be made in a separate step in which case the anvil 10 does not need to have a sharp distal end. The hole which is formed in the wall of the target vessel 42 by the anvil arm 14 is preferably small enough to prevent significant bleeding through the puncture site. The hole is preferably less than 2 mm, and more preferably less than 1 mm in width. The anvil arm 14 also preferably has a substantially uniform cross-section along its length to allow for puncture of the vessel and insertion through the vessel wall yet still capable of providing support to the tissue of the vessel during anastomosis. The anvil arm 14 is depicted as being round in cross-section in FIG. 2A but other cross sectional shapes may be used such as polygonal, ovoid, etc. One example of an anvil arm 14 according to the present invention has a height and a width of about 2 mm or less, preferably about 1 mm or less, and a length of about 2 to 15 mm, preferably 5 to 12 mm. The length of the anvil arm 14 will vary depending on the diameter of the graft vessel selected. Preferably, a length to width ratio of the anvil arm 14 is between 2:1 and 15:1.

Figure 2B:
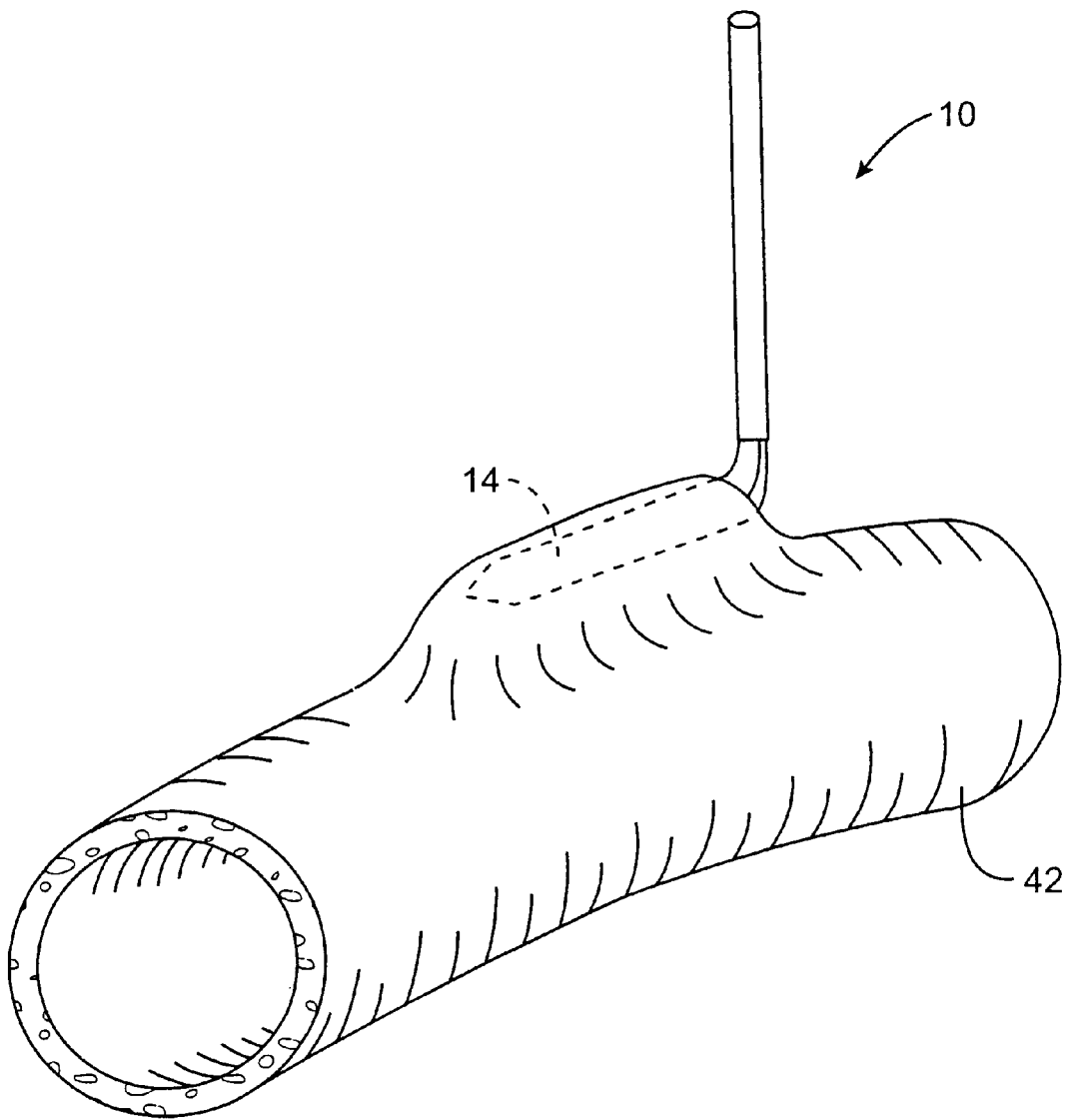
FIG. 2B is a perspective view of the anvil tenting a wall of a target vessel for an anastomosis procedure.

Once the anvil arm 14 has been inserted into the target vessel 42, the anvil arm 14 is pulled against an inner wall of the target vessel causing tenting of the thin tissue of the vessel wall as illustrated in FIG. 2B. This tenting of the vessel wall provides control over the anastomosis site during an anastomosis procedure. During tenting of the target vessel 42, the upper or tissue contacting surface of the anvil is brought into contact with the tissue on the interior of the target artery.

Figure 3A:
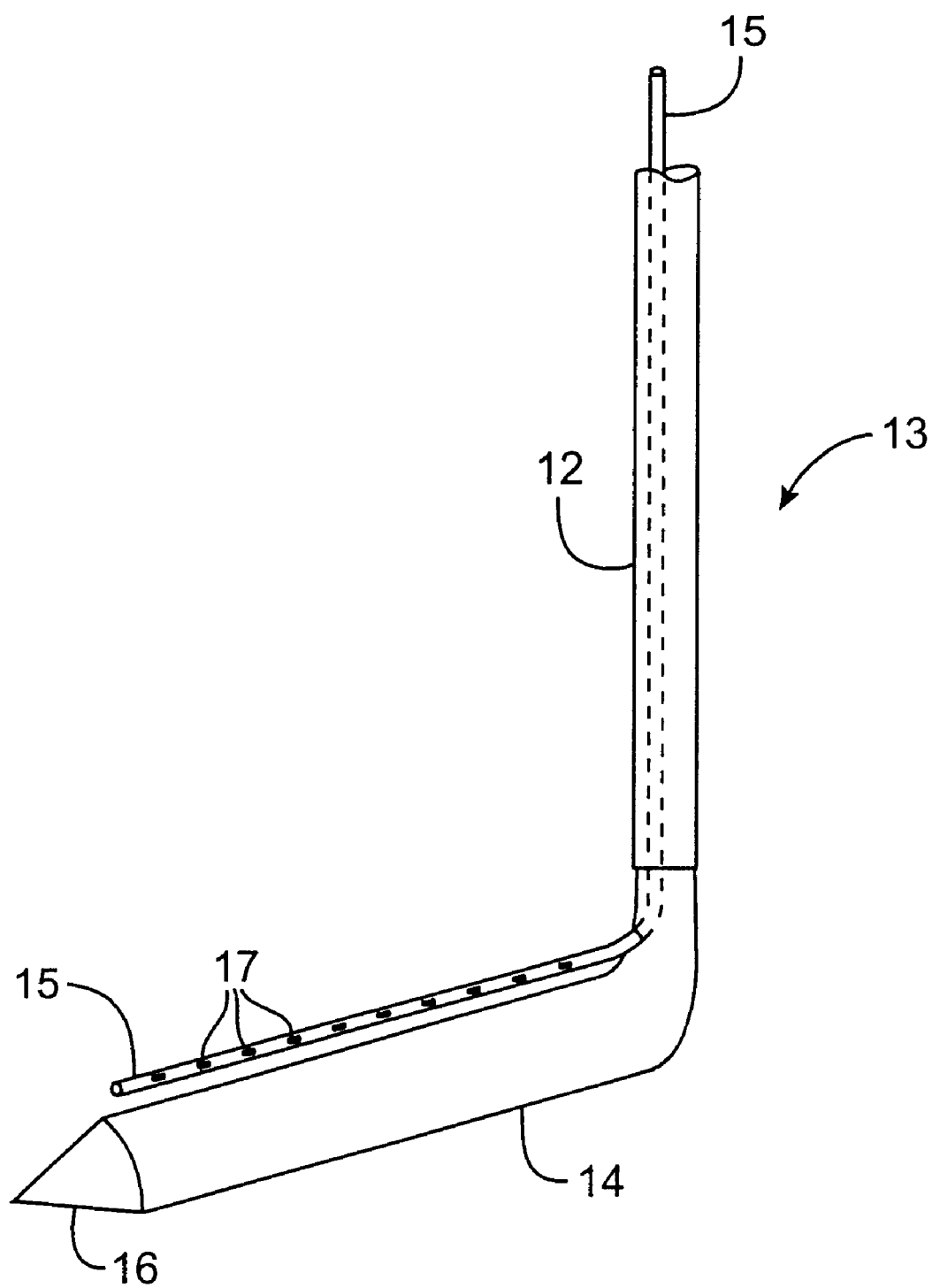
FIG. 3A is a perspective view of an anvil according to one embodiment of the present invention having a tissue adhesive applicator tube.

In FIG. 3A, an anvil 13 is shown having an external applicator for supplying a tissue adhesive to the bond region. The applicator includes a tube 15 with two sets of holes 17 on opposite sides of the tube. The tube is threaded through a hole in the handle 12 to an internal or external adhesive supply (not shown). The applicator tube 15 is spaced from the anvil arm such that when the anvil arm 14 is inserted in a target vessel, the applicator tube remains external to the target vessel. In use, adhesive is forced down the tube 15 and emerges through the holes 17 in the applicator tube. The adhesive can be applied before or after the graft vessel is brought into position for anastomosis. In an alternative embodiment, the external glue applicator can be part of an external cutter assembly for forming an incision in the target vessel.

Figure 3B:
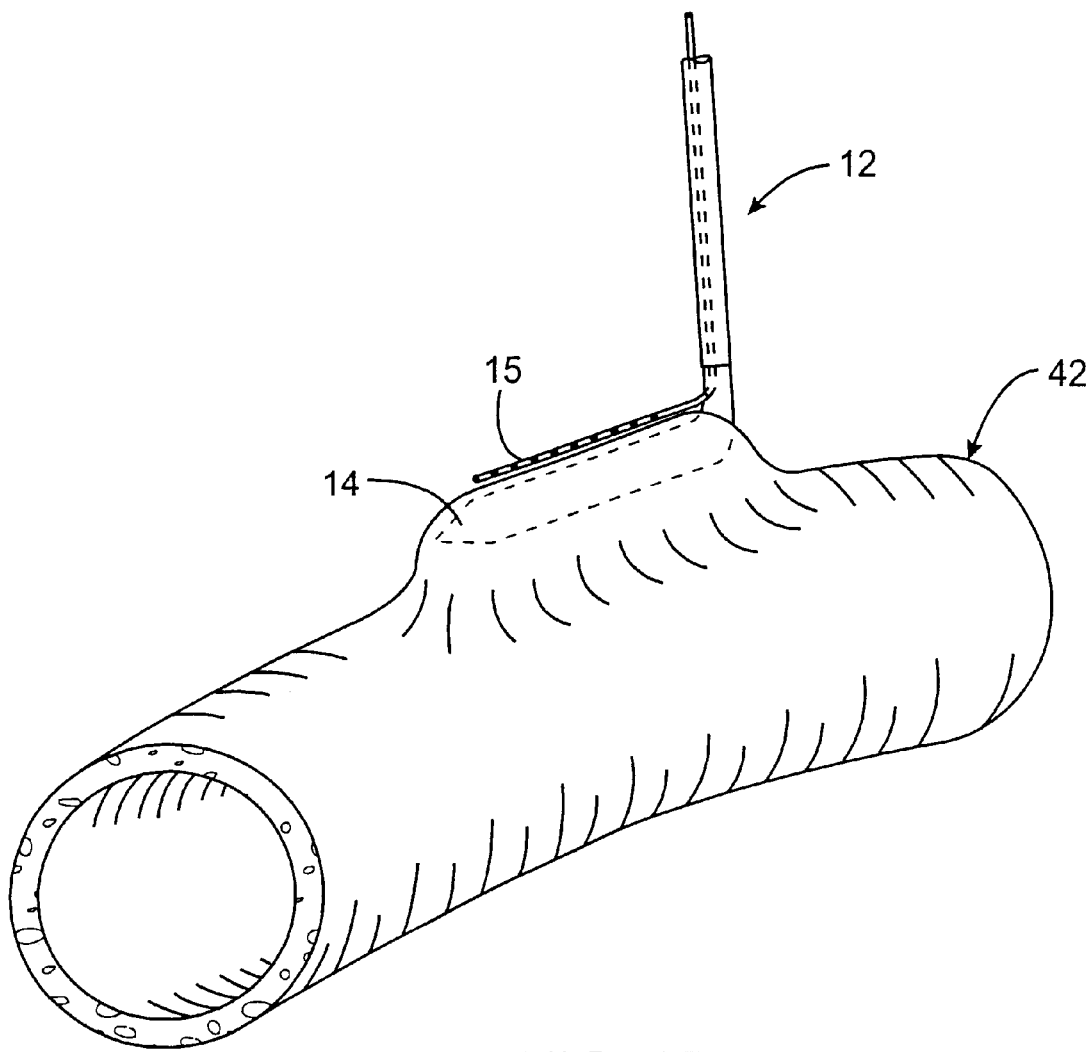
FIG. 3B is a perspective view of the anvil of FIG. 3A tenting a wall of a target vessel for an anastomosis procedure.

FIG. 3B shows the anvil of FIG. 3A inserted into the wall of a target vessel 42. As shown, the applicator tube 15 is in position on the exterior of the target vessel 42 to deliver adhesive to the bond region on either side of the applicator tube 15.

Figure 4A:
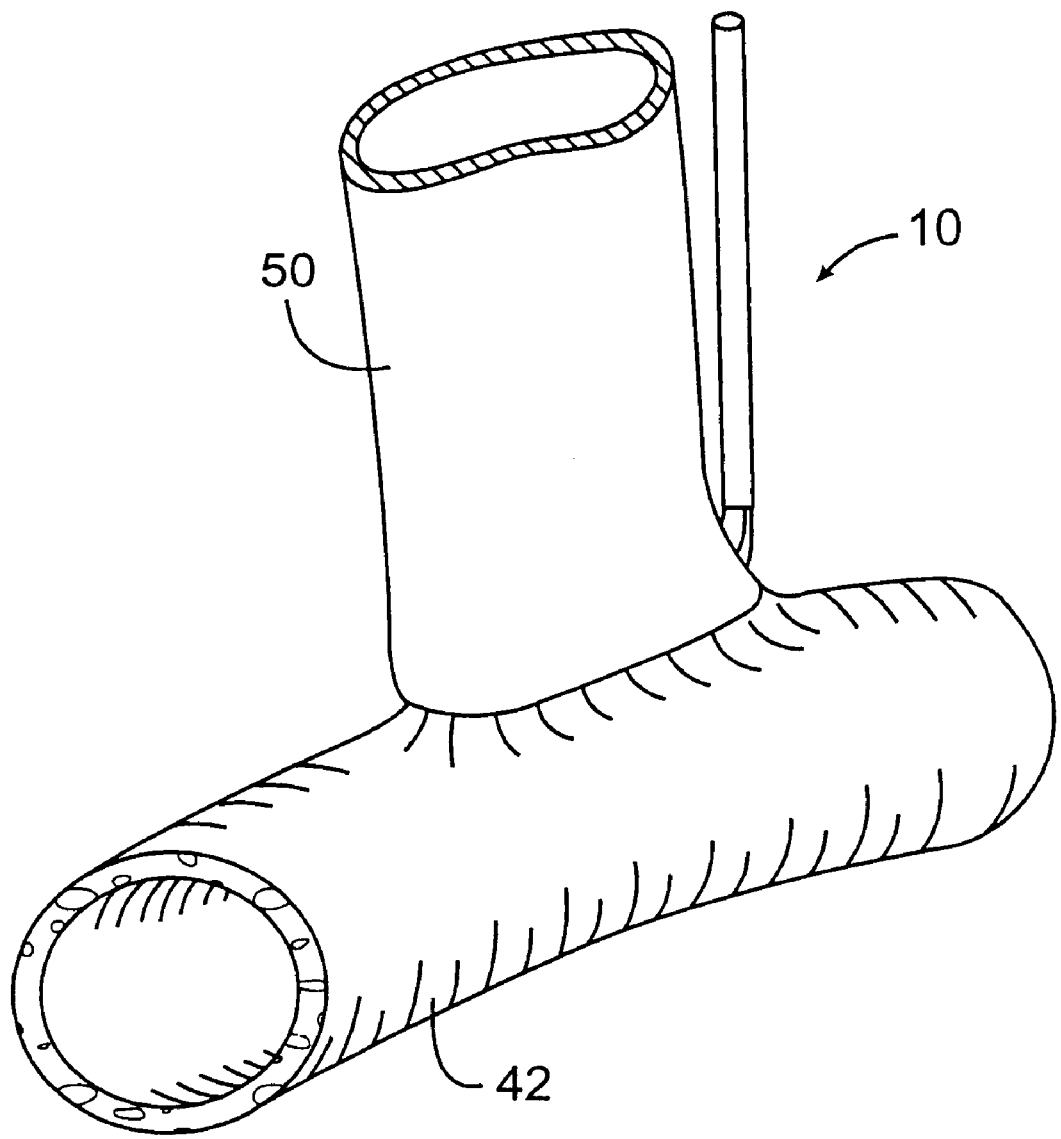
FIG. 4A is a perspective view of a graft vessel placed adjacent an exterior of the tented target vessel for the anastomosis procedure.
Figure 4B:
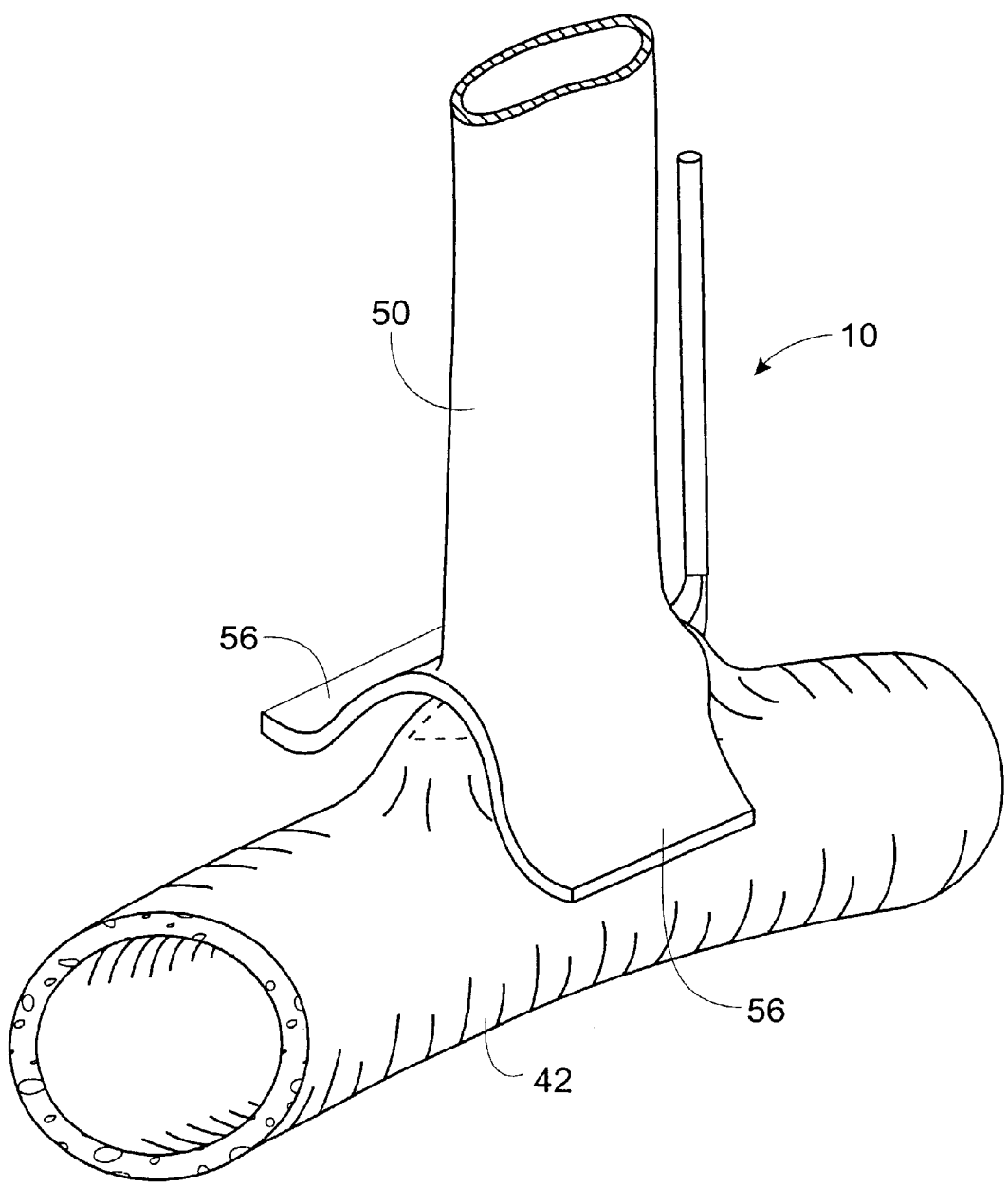
FIG. 4B is a perspective view of a graft vessel placed adjacent an exterior of the tented target vessel for the anastomosis procedure wherein the end of the graft vessel has been split to form two graft vessel flaps.

FIG. 4A shows a graft vessel 50 positioned adjacent an exterior of the target vessel 42 at the anastomosis site. In FIG. 4B, an alternative embodiment is shown where an end of the graft vessel 50 has been split in preparation for grafting to form two graft vessel flaps 56. The tented portion of the target vessel 42 is positioned inside the graft vessel 50 in the step of FIG. 4B with one of the graft vessel flaps 56 on either side of the anvil 10.

With the graft vessel positioned as shown in FIG. 4A or 4B, a graft vessel fixture can then be employed to compress the graft vessel tissue against the anvil in preparation for tissue welding. The graft vessel fixture includes at least two clamping members having clamping surfaces which compress the graft and target vessel tissue against opposing portions of the anvil on opposite sides of the graft vessel. The graft vessel may be mounted in the fixture prior to positioning the graft vessel against the target vessel. Alternatively, the graft vessel can be positioned against the wall of the target vessel before the graft vessel fixture is brought into position.

Figure 5A:
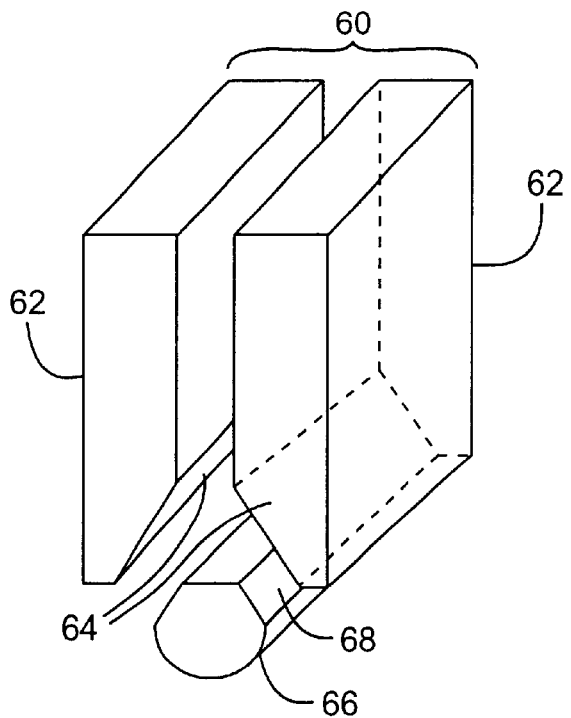
FIG. 5A is a perspective view of an anastomosis system including a graft vessel fixture having angled clamping surfaces and a corresponding anvil.

The clamping members of the graft vessel fixture can have various forms. FIG. 5A shows a system for performing anastomosis comprising a graft vessel fixture 60 having clamping members 62 with angled clamping surfaces 64. An anvil 66 having corresponding angled surfaces 68 is also shown in FIG. 5A. To effectuate tissue welding, the clamping surfaces 64 of the clamping members 62 can be provided with energy applying surfaces such as electrodes for RF power application, exposed optical fiber ends for laser energy application, or vibrating surfaces for ultrasonic power application.

Figure 5B:
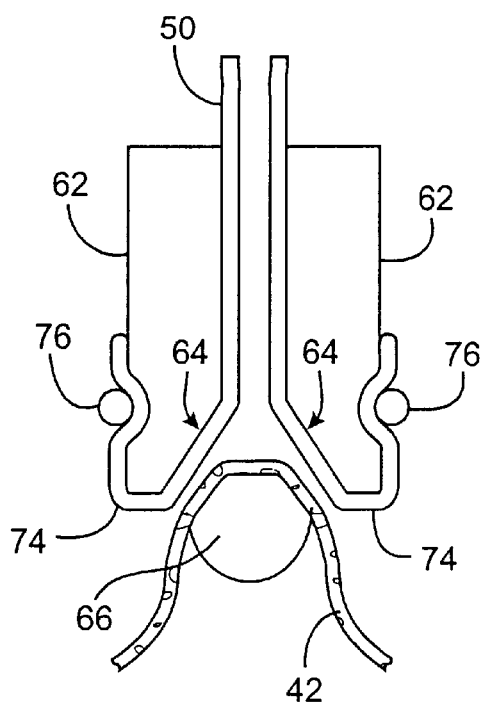
FIG. 5B is a cross-sectional view of graft and target vessels mounted in the system of FIG. 5A.

FIG. 5B shows a cross-sectional view of the system of FIG. 5A with the graft vessel 50 and target vessel 42 in position for clamping. As shown, the end of the graft vessel 50 has been split to form two graft vessel flaps 56 which are held in position against the clamping members 62 by pins 76.

When tissue bonding is accomplished with RF energy, the energy applying surfaces on the graft vessel fixture comprise one or more electrodes. The electrodes can be either continuous or segmented. In the case of the fixture having angled clamping surfaces 64 as shown in FIG. 5A, the electrodes are preferably arranged as vertical strips (oriented in the graft vessel direction) or horizontal strips (oriented in the target vessel direction). The use of vertical strips is particularly preferred since it allows for less precision in the positioning of the fixture. The vertical strips can also be used to reduce or minimize the flap of unbonded target vessel tissue adjacent the incision formed in the target vessel wall.

Figure 6A:
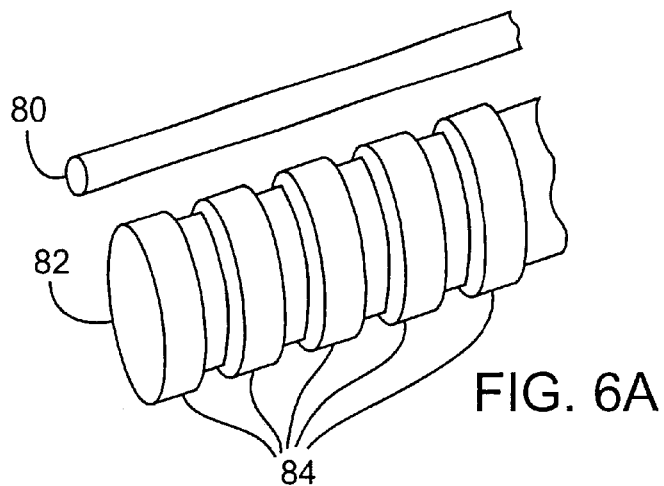
FIG. 6A is a perspective view of an anastomosis system with an anvil having projections.
Figure 6B:
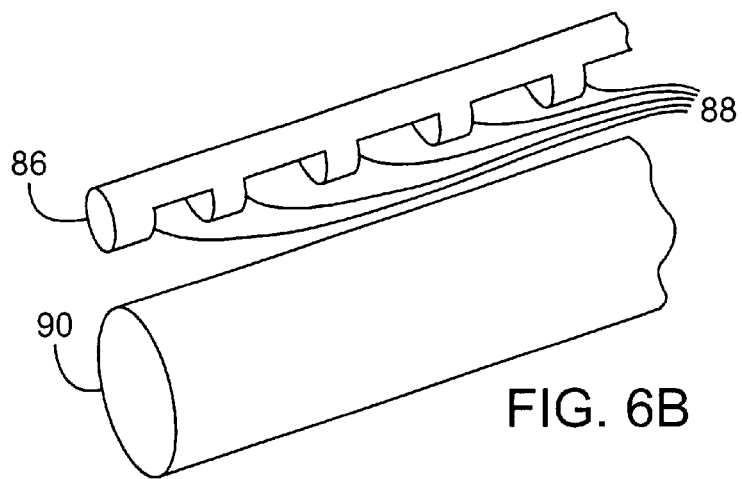
FIG. 6B is a perspective view of an anastomosis system with a clamping member having projections.
Figure 6C:
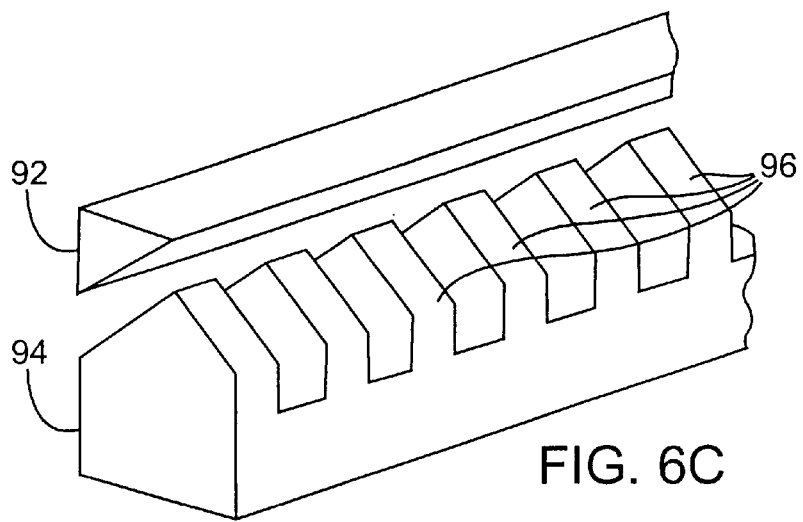
FIG. 6C is a perspective view of an anastomosis system with a clamping member and an anvil having angled clamping surfaces and projections.

Various clamping member and anvil arrangements are shown in FIGS. 6A–6C. These arrangements are particularly suitable for use with RF tissue welding. For purposes of clarity, only one clamping member is shown.

FIG. 6A shows an embodiment wherein the clamping members 80 comprise two parallel arms or pins which serve as electrodes and which form two elongated clamping surfaces with the anvil 82. As shown, the anvil 82 has a plurality of projections 84. In the case of RF tissue welding, each of these projections 84 can be electrically isolated and powered separately by conductors threaded through the interior of the anvil arm.

FIG. 6B shows an embodiment wherein the clamping members 86 comprise a plurality of projections 88 each of which forms a separate clamping surface with the anvil 90. In the case of RF welding, each of these projections 88 can be electrically isolated from the other projections so that power can be applied sequentially to individual electrode projections.

FIG. 6C shows a clamping member 92 having a triangular cross-section and a corresponding anvil 94 having angled tissue contacting surfaces with projections 96.

The clamping surfaces can also be provided with teeth-like projections having triangular cross-sections or with projections having other cross-sectional shapes. Further, the projections can be provided on both the clamping surfaces of the clamping members and the tissue contacting surfaces of the anvil. The projections on the anvil and/or clamping members can help to increase the surface area in the bond region thus increasing bond strength. The projections can also provide mechanical interlocking of the graft and target vessel tissue. Clamping pressure can be applied before, during and/or after the application of welding energy to improve tissue weld formation.

In the case of RF tissue welding, the external electrodes can also be provided with sharp spikes which become embedded in the graft vessel tissue when the graft and target vessels are clamped together. The spikes in the electrodes become embedded in the target vessel tissue during clamping and allow the RF energy to be applied closer to the interface between the graft and target vessels.

Figure 7A:
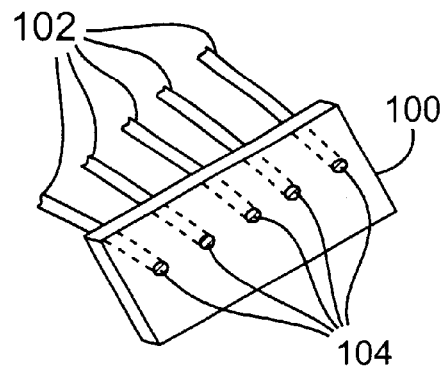
FIG. 7A is a perspective view of the tissue contacting surface of a fiber holding plate.

In the case of laser welding, the clamping surfaces of the graft fixture can comprise a fiber holding plate or a laser stencil. An example of a fiber holding plate is shown in FIG. 7A. FIG. 7A is a view of the front or tissue clamping surface of the fiber holding plate 100. The fiber holding plate 100 includes a plurality of optical fibers 102 having ends 104 exposed at the tissue contacting surfaces of the fiber holding plate.

Figure 7B:
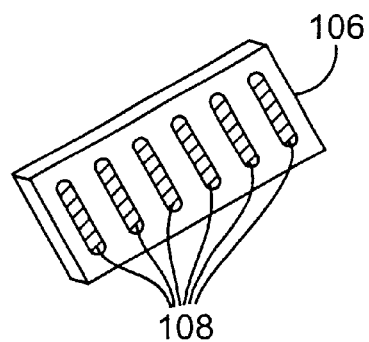
FIG. 7B is a perspective view of one embodiment of a laser stencil according to the present invention.
Figure 7C:
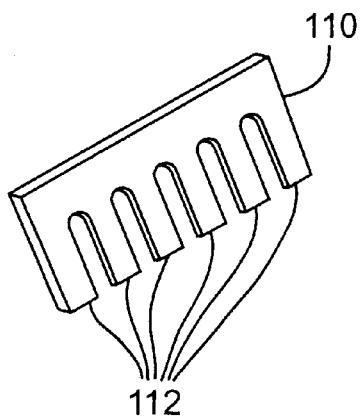
FIG. 7C is a perspective view of a second embodiment of a laser stencil according to the present invention.

In an alternative embodiment, the external clamping surfaces can be in the form of a laser stencil. Two embodiments of a stencil are shown in FIGS. 7B and 7C. In FIG. 7B, a laser stencil 106 is shown having elongated openings 108 in a central portion thereof. The openings allow the laser energy to contact exposed portions of the underlying tissue. In FIG. 7C, a comb shaped stencil 110 is shown having projections 112 which form openings therebetween. In use, a powered laser is moved across the laser stencil to create welds in the underlying tissue.

In the case of ultrasonic welding, the clamping surfaces can be provided with a device similar to the fiber plate discussed above wherein the optical fibers have been replaced with wires which can be used to transmit ultrasonic energy. Alternatively, the clamping surfaces can be provided with projections and the entire clamping surface can be vibrated. The ultrasonic energy can be produced by means of ultrasonic transducers such as piezo-electric stacks or magneto-restrictive elements or by other means known in the art.

Ultrasonic or vibrational energy can also be used in combination with other tissue welding techniques such as RF or laser welding. By vibrating the anvil and/or clamping surfaces before, during or after tissue welding, improved tissue welds can be formed.

In the case of adhesive bonding, the adhesive can be applied to the tissue mating surfaces of the graft and/or target vessels before the surfaces are brought into contact. The adhesive may be applied to either or both of the mating surfaces of the graft and target vessels. The adhesive may be a one part or a two part adhesive. Further, the curing of the adhesive may be activated by light or heat energy. The adhesive may be applied as a liquid or as a solid film. Preferred adhesive materials include collagen, albumin, fibrin, hydrogel and glutaraldehyde. Other adhesives such as cyano-acrylates may also be used.

In an alternative embodiment, the tissue mating surfaces can be brought into position for anastomosis before the tissue adhesive is applied to the interface region between the graft and target vessels. This procedure is particularly preferred when fast curing adhesives such as certain of the cyano-acrylates are employed. The adhesive can be supplied to the mating surfaces through holes made in the graft vessel in a previous step. Alternatively, the adhesive may be injected through the graft vessel tissue using one or more needles as shown in FIG. 8A.

Figure 8A:
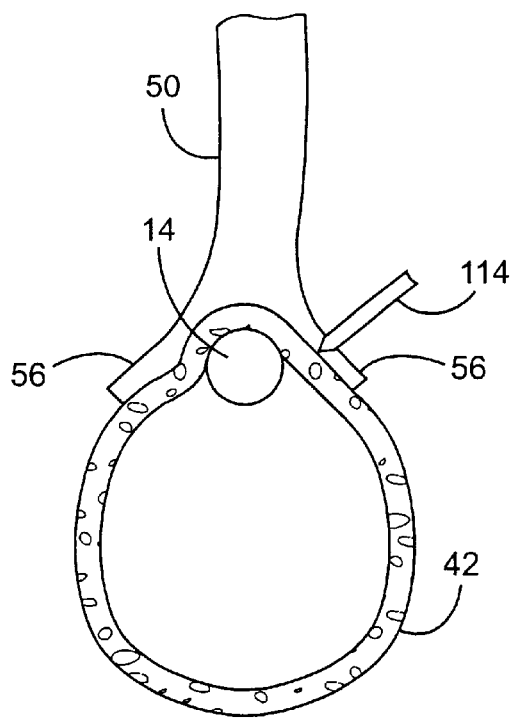
FIG. 8A is a cross-sectional view showing a graft and target vessel in position for anastomosis wherein a needle for injecting a tissue adhesive is inserted through the graft vessel flap.

FIG. 8A shows a cross-sectional view of a graft vessel 50 and target vessel 42 in position for anastomosis. As shown, the target vessel 42 is tented by an anvil 14 and the end of the graft vessel 50 has been split to form two graft vessel flaps 56. A needle 114 is shown inserted through one of the graft vessel flap such that a tissue adhesive can be injected into the interface between the graft and target vessel. Although only one needle is shown, a plurality of needles can be simultaneously deployed on either side of the graft vessel to form spot bonds. Additionally, external clamping members can be deployed against the anvil surfaces before, during, and/or after the adhesive has been injected to improve the bond strength.

Figure 8B:
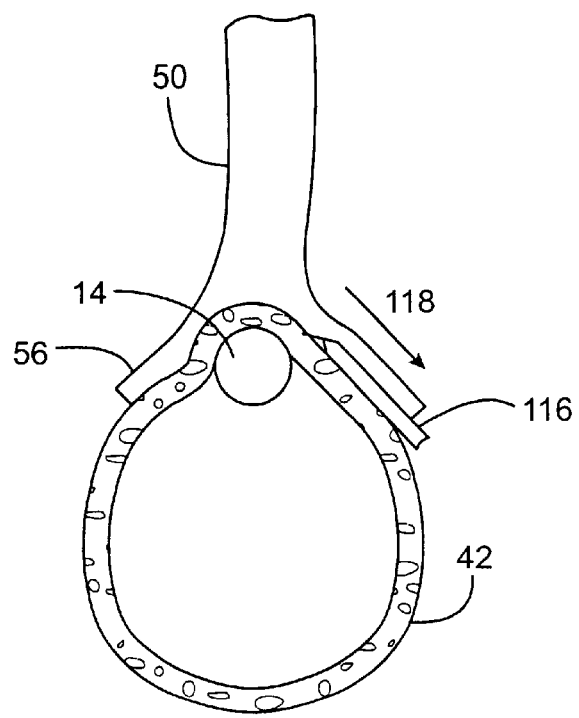
FIG. 8B is a cross-sectional view showing a graft and target vessel in position for anastomosis wherein a needle for injecting a tissue adhesive is inserted under the graft vessel flap.

FIG. 8B shows an alternative embodiment wherein a needle 116 is inserted under the graft vessel flap. Although a needle is shown, a flexible tube may also be used to facilitate removal of the adhesive applicator. As with the embodiment of FIG. 8A, a plurality of needles or flexible tubes can be deployed on either side of the graft vessel 50. The adhesive can be injected while the needle or tube is being retracted in the direction 118 to form adhesive bond lines. As with the embodiment of FIG. 8A, external clamping members can be deployed to clamp the graft and target vessel tissue against the anvil surfaces before, during, and/or after adhesive has been injected.

Figure 9A:
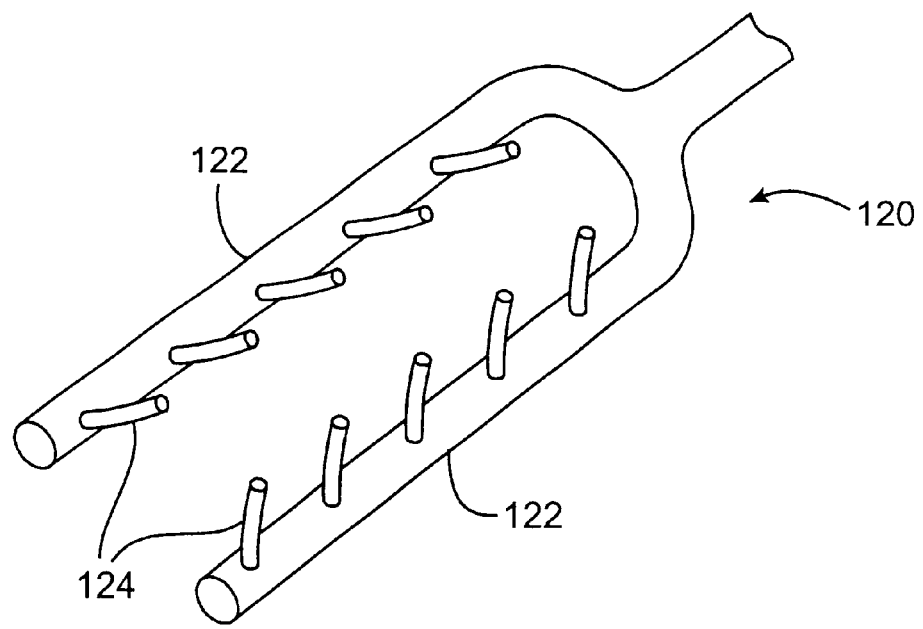
FIG. 9A is a perspective view of a first embodiment of a pin assembly for a graft vessel fixture comprising adhesive applicator tubes.

The adhesive applying needles or tubes may be a part of a graft vessel fixture or clamp as shown in FIGS. 9 and 10. In FIG. 9A, a pin assembly 120 for a graft vessel fixture is shown comprising two parallel arms 122 for trapping the graft vessel against clamping members (not shown). The parallel arms 122 include a plurality of tubes 124 for supplying a tissue adhesive to the bond region. The adhesive supplying tubes 124 extend upwardly and inwardly from each of the parallel arms 122. The tubes 124 may be flexible to facilitate removal after the anastomosis procedure has been performed.

Figure 9B:
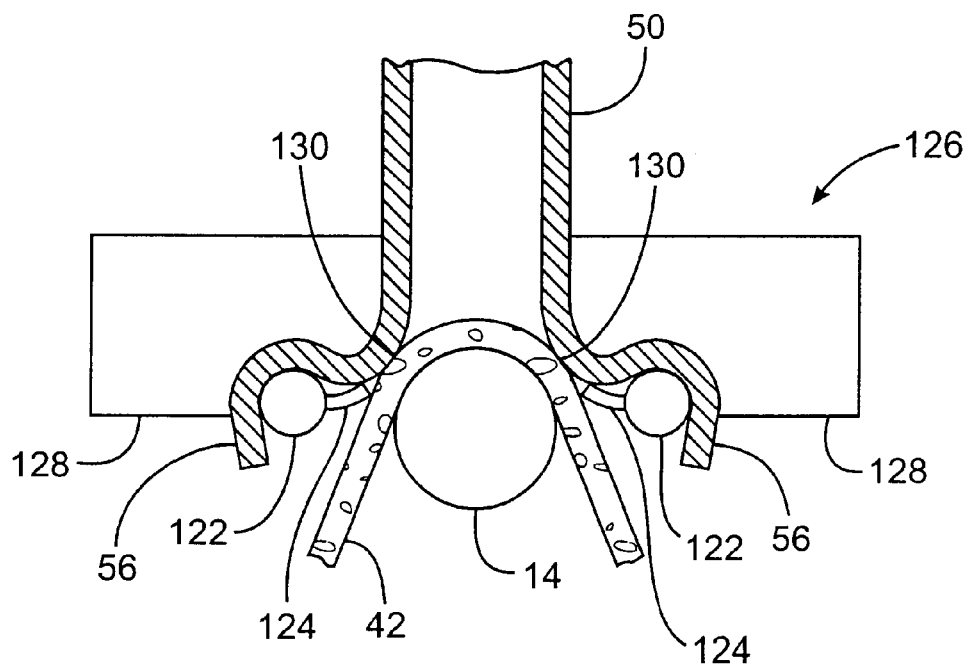
FIG. 9B is a cross-sectional view of a graft vessel fixture comprising the pin assembly of FIG. 9A in position for anastomosis.

FIG. 9B is a cross-sectional view of a graft vessel fixture 126 comprising the pin assembly 120 of FIG. 9A in position for an anastomosis procedure. An anvil arm 14 is shown tenting the wall of the target vessel 42. As shown, the parallel arms 122 of the pin assembly 120 trap the flaps 56 of a graft vessel 50 against clamping members 128 of the fixture 126. The adhesive applicator tubes 124 extend from the parallel arms 122 upwardly and inwardly such that an adhesive injected through the tubes is deposited in the bond region 130.

Figure 10A:
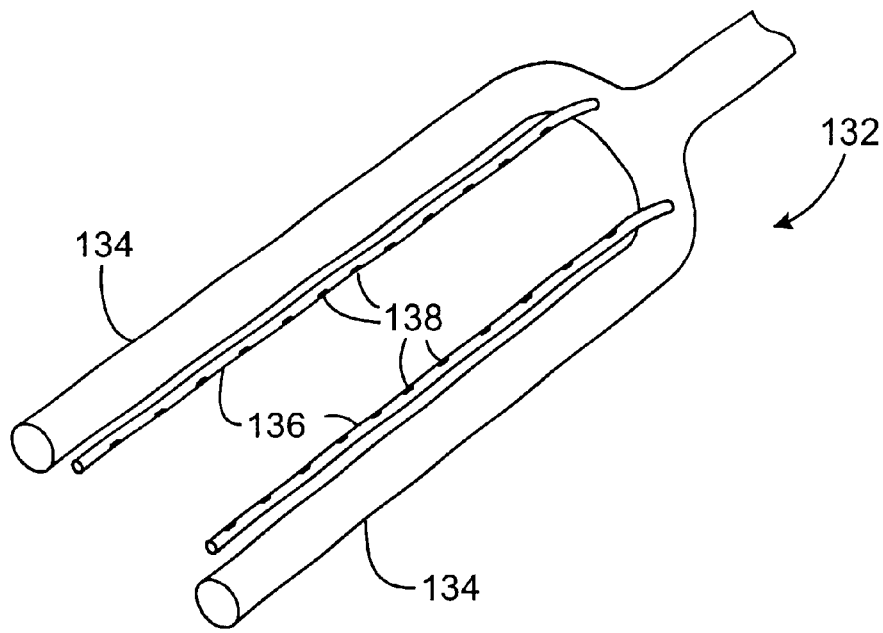
FIG. 10A is a perspective view of a second embodiment of a pin assembly for a graft vessel fixture comprising adhesive applicator tubes.

In FIG. 10A an alternative embodiment of a pin assembly for a graft vessel fixture is shown. The pin assembly 132 comprises two parallel arms 134 each of which is provided with an adhesive applicator tube 136. The adhesive applicator tubes 136 extend parallel to the parallel arms 134 of the pin assembly 132. The tubes 136 are provided with a plurality of holes 138.

Figure 10B:
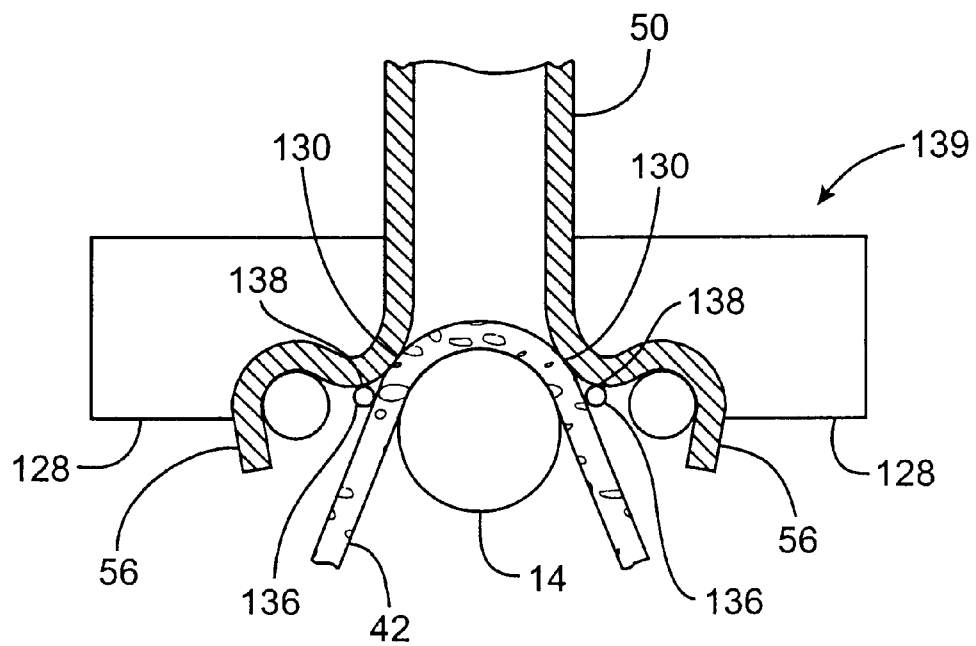
FIG. 10B is a cross-sectional view of a graft vessel fixture comprising the pin assembly of FIG. 10A in position for anastomosis.

FIG. 10B is a cross-sectional view of a graft vessel fixture 139 comprising the pin assembly 120 of FIG. 10A in position for an anastomosis procedure. An anvil arm 14 is shown tenting the wall of the target vessel 42. As shown, the parallel arms 134 of the pin assembly 132 trap the flaps 56 of a graft vessel 50 against clamping members 128 of the fixture 126. The adhesive applicator tubes 136 extend parallel to the arms 122 of the fixture with the holes 138 oriented such that an adhesive injected through the tubes is deposited in the bond region 130.

According to one preferred embodiment of the invention, after tissue bonding has been completed, an incision is formed in the wall of the target vessel to allow blood flow between the target vessel and the graft vessel. The incision may be made before or during withdrawal of the anvil arm from the target vessel. The withdrawal of the anvil arm preferably leaves only a small gap in the target vessel and therefore only minimal blood leakage occurs at the location where the anvil arm has been withdrawn.

Various cutting devices may be used to make the incision in the target vessel according to the present invention. Suitable cutting devices, for example, are disclosed in U.S. patent application Ser. No. 09/363,255, entitled "Anastomosis System and Method of Controlling a Tissue Site", filed Jul. 28, 1999. Cutting devices which are either internal or external to the anvil may be employed. In a preferred embodiment, the cutting device can be an electro-cautery cutting device electrically connected to a power source to form an electrode. By causing electric current to flow through the tissue between the electrode surfaces on the anvil and the cutting device, the incision can be cauterized. The cautery action can cause the tissue surrounding the incision to shrink thereby opening up the incision in the target vessel and thus allowing for increased blood flow between the target and graft vessels.

Figure 11:
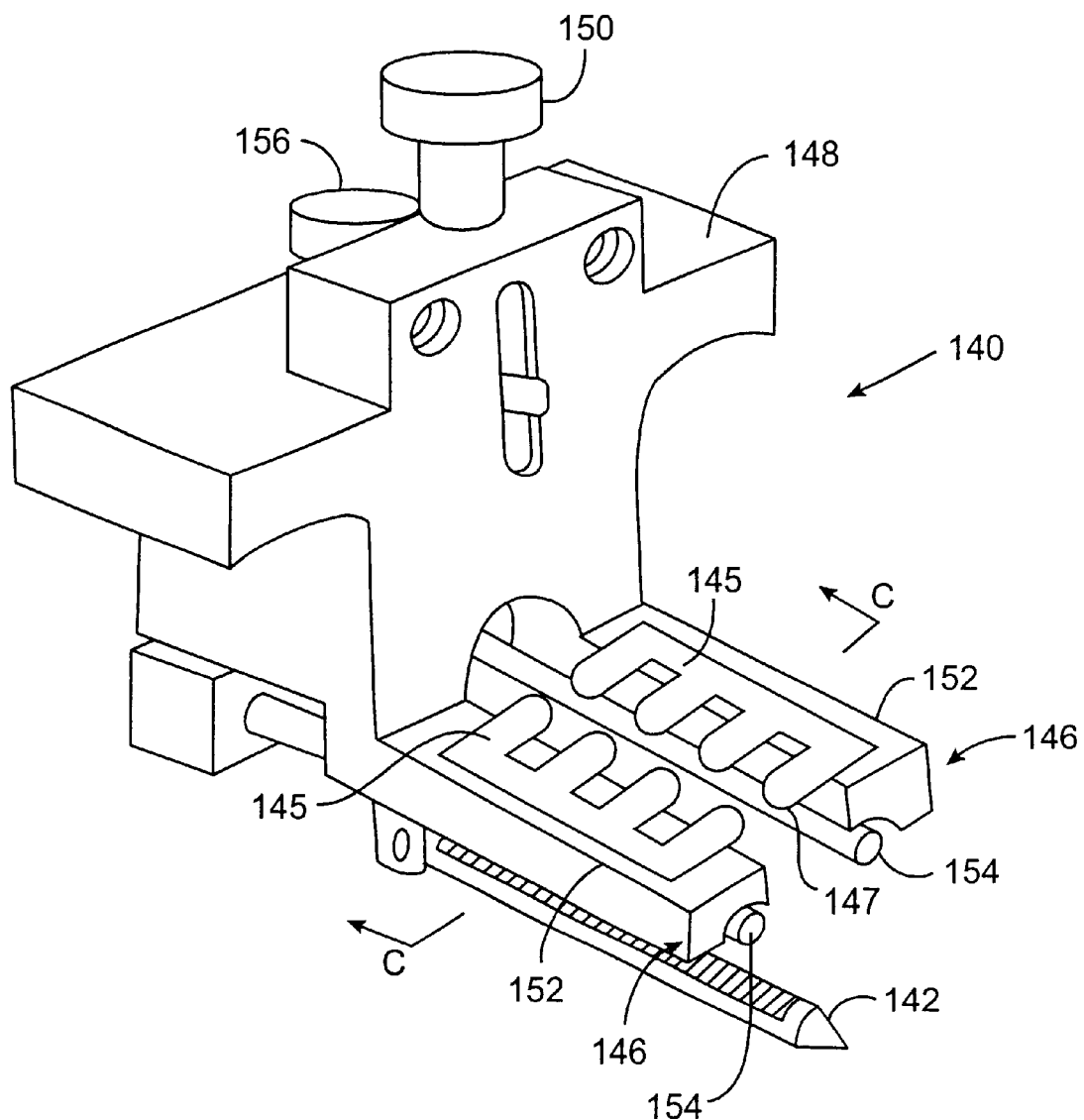
FIG. 11 is a perspective view of a system for controlling a tissue site and performing anastomosis according to the present invention.

FIG. 11 shows an embodiment of a system 140 for controlling a tissue site and performing anastomosis according to one embodiment of the present invention. The system shown uses RF energy to accomplish tissue welding. However, the system could be adapted for other tissue bonding techniques such as laser welding, ultrasonic welding or adhesive bonding.

The system 140 includes an anvil 142 and a graft vessel holder 146 all mounted on a handle 148. For purposes of clarity, the cutter is not shown. The anvil 142 is mounted on the handle 148 and connected to an actuator 150 which allows the anvil to be moved downward against the bias of a spring inside the handle. The cutter 144 may be spring biased or fixed and is positioned on the handle 148 directly above the anvil 142. The graft vessel holder 146 includes two fixed arms 152 and two movable arms 154. The two movable arms 154 are connected to a second actuator 156 on the handle 148. Depression of the second actuator 156 against the bias of a spring within the handle 148 causes the movable arms 154 to be moved downward away from the fixed arms to receive portions of a graft vessel between the movable and fixed arms. Electrodes 145 are mounted on the fixed upper arms 152 of the graft vessel holder 145. These electrodes 145 have projections 147 extending inwardly toward the opposite fixed arm of the graft vessel holder 146. In use, each of the projections 147 forms a clamping surface with the anvil 142.

Figure 12A:
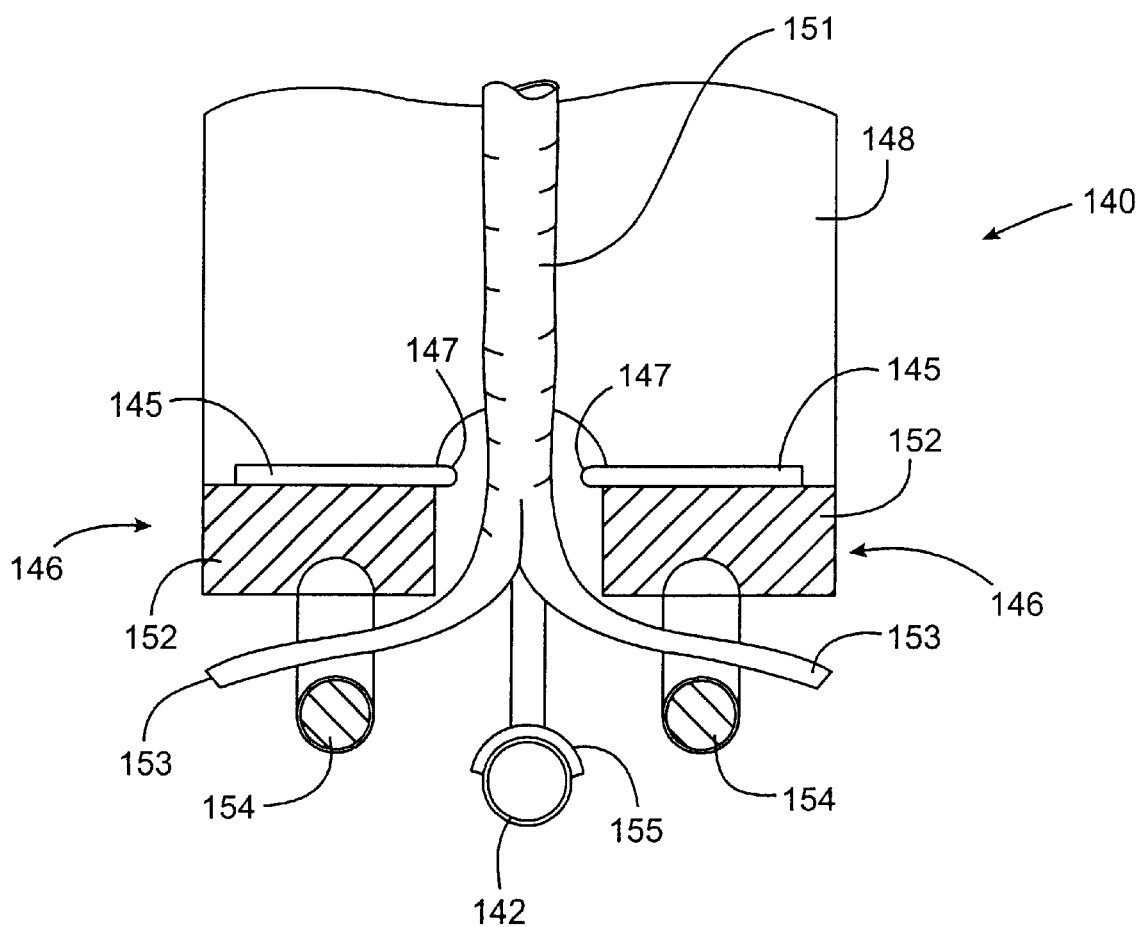
FIG. 12A is a cross sectional view taken along line C—C of FIG. 11, showing a first step of the anastomosis procedure.
Figure 12B:
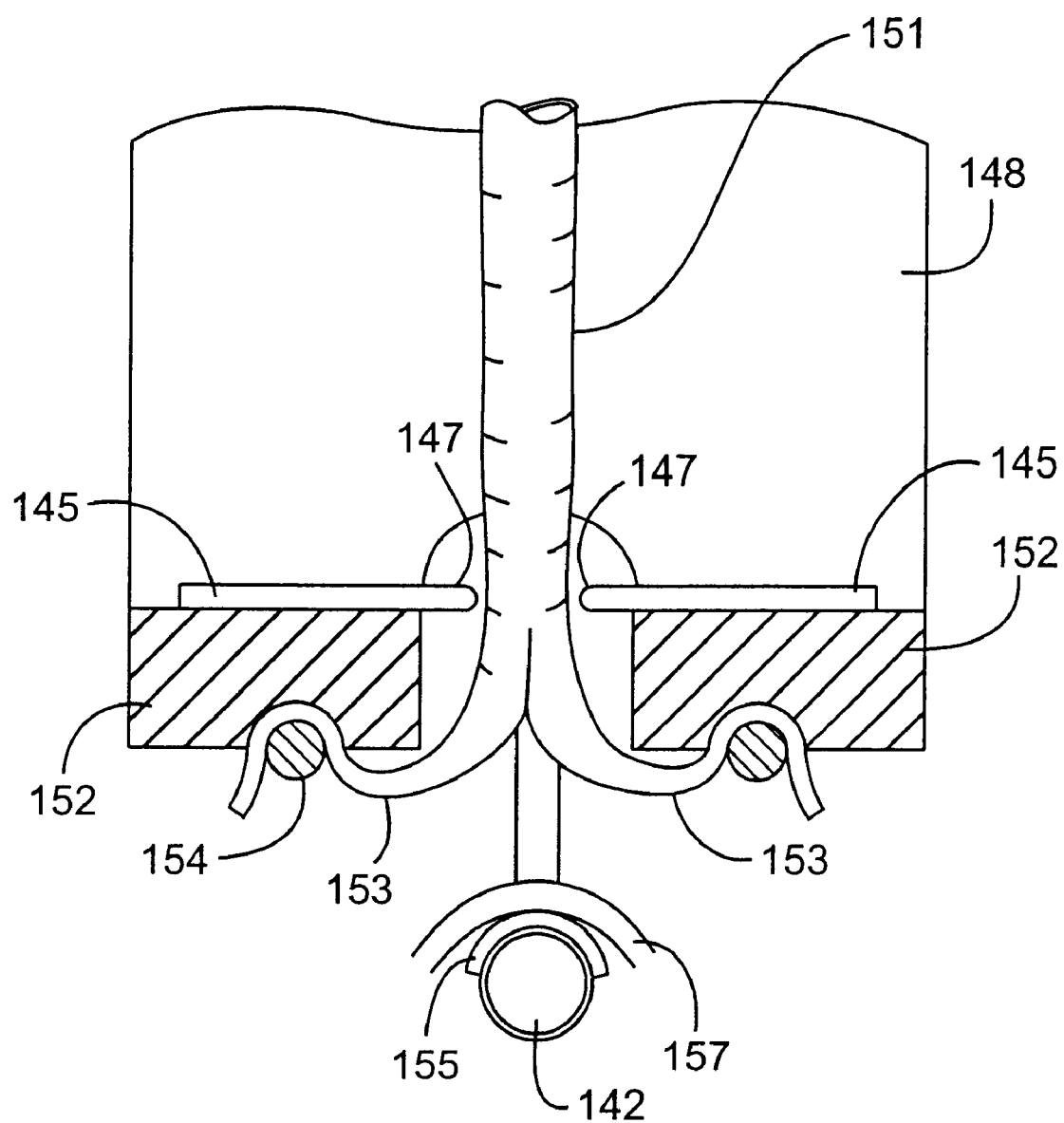
FIG. 12B is a cross sectional view taken along line C—C of FIG. 11, showing a second step of the anastomosis procedure.
Figure 12C:
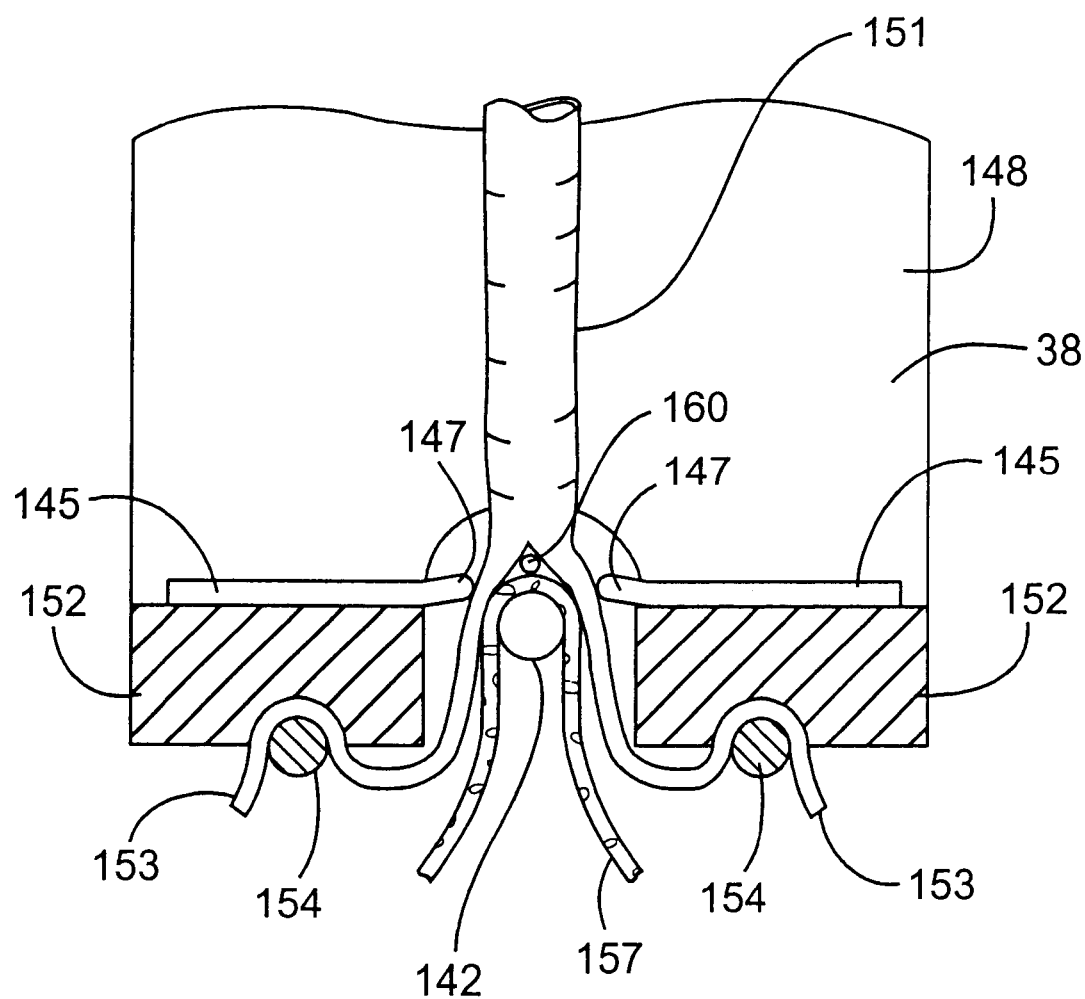
FIG. 12C is a cross sectional view taken along line C—C of FIG. 11, showing a third step of the anastomosis procedure.

The operation of the system 140 of FIG. 11 is shown in the cross sectional views of FIGS. 12A–12C. As shown in FIG. 12A, an end of a graft vessel 151 has been split to form two graft vessel flaps 153 which can be held in position by the graft vessel holder 146. In order to load the graft vessel 151 into the system 140, the first actuator 150 and the second actuator 156 are depressed to move the anvil 142 and the movable arms 154 downward. The split graft vessel 151 is then inserted between the fixed and movable arms 152 and 154 and the second actuator 156 is released to trap the flaps 153 of the graft vessel 151, as shown in FIG. 12B. The anvil 142 having an electrode surface 155 is then inserted into the target vessel 157 as described above with respect to the various other anvil embodiments.

Once the anvil 142 has been inserted in the target vessel 157 as shown in FIG. 12B, the actuator 150 is released to allow the anvil to move upward to tent the wall of the target vessel 157. The electrode surface 155 of the anvil 142 is thus brought into contact with the interior wall of the target vessel 157. FIG. 12C illustrates the tented target vessel 157 positioned adjacent the split and trapped graft vessel 151 in a position for performing anastomosis. The projections of the external electrodes 147 are now in contact with the external wall of the graft vessel 151. The external and internal electrodes 147 and 155 are connected to the opposite poles of a power source such as a bipolar RF generator. Power is then applied to either the internal or external electrodes causing current to flow through the tissue compressed between the external and internal electrodes to weld the graft and target vessels together. Once the tissue welding is complete, the anvil 142 is removed and the incision in the target vessel is made. The incision can be made during withdrawal of the anvil 142 by an electro-cautery cutting device 160 as described above.

The above system can be modified for different internal/external electrode configurations as set forth above. Furthermore, either the internal or external electrodes can be powered with the other electrode or electrodes serving as the return.

The above system can also be adapted for laser or ultrasonic tissue welding by replacing the external electrodes with a fiber or wire holding plate. Alternatively, in the case of laser tissue welding, the anvil can be provided with optical fibers having ends exposed at a tissue contacting surface thereof.

In the case of tissue welding, the tissue welds may be strengthened by the use of known fillers (e.g., collagen or albumin) or adhesives which can be activated by the heat generated during the tissue welding procedure. The adhesive or filler may be placed between the graft and target vessel tissue surfaces prior to apposition in the form of a liquid or strips of a solid adhesive film. Alternatively, the tissue adhesive or filler can be injected after tissue apposition in a manner as set forth in FIGS. 8–10.

While the invention has been described in detail with reference to the preferred embodiments thereof, it will be apparent to one skilled in the art that various changes and modifications can be made and equivalents employed, without departing from the present invention.

What is claimed is:

1. A method of performing anastomosis comprising steps of:
providing an anastomosis system comprising an elongated anvil and a graft vessel fixture movable with respect to said anvil, said graft vessel fixture comprising clamping members each having one or more clamping surfaces adapted to compress the tissue on opposite sides of the graft vessel against tissue contacting surfaces of the anvil;
inserting the elongated anvil through the wall of a target blood vessel and positioning the elongated anvil along an interior of the target blood vessel wall;
positioning an end of a graft vessel adjacent an exterior of the target blood vessel wall;
moving the fixture toward the anvil to compress the graft and target vessel tissue between the anvil and the clamping surfaces of the fixture; and
applying energy to the tissue compressed between the anvil and the clamping surfaces of the fixture to secure the graft and target vessels together.

2. The method of claim 1, further comprising steps of:
making an opening in the target vessel to allow blood to flow between the target vessel and the graft vessel; and
removing the anvil.

3. The method according to claim 1, wherein the anvil and the clamping surfaces of the graft vessel fixture comprise one or more electrodes and wherein the tissue welds are formed by applying RF energy via the electrodes to the compressed tissue.

4. The method according to claim 1, wherein the anvil comprises a plurality of optical fibers having ends which are exposed at a tissue contacting surface thereof and wherein the tissue welds are formed by applying laser energy via the optical fibers to the compressed tissue.

5. The method according to claim 1, wherein the clamping surfaces of the graft vessel fixture comprise optical fibers having ends which are exposed at tissue contacting surfaces thereof and wherein the tissue welds are formed by applying laser energy via the optical fibers to the compressed tissue.

6. The method according to claim 1, wherein the clamping members of the graft vessel fixture comprise wires having ends which are exposed at the clamping surfaces thereof and wherein the tissue welds are formed by applying ultrasonic energy via the wires to the compressed tissue.

7. The method according to claim 3, wherein the electrodes on the graft vessel fixture comprise a plurality of projections each of which forms a separate clamping surface with the anvil.

8. The method according to claim 3, wherein the anvil comprises a plurality of projections each of which forms a separate clamping surface with the graft vessel fixture.

9. The method according to claim 7, wherein one or more of the projections are electrically isolated from the rest of the projections and wherein current is supplied sequentially to each electrically isolated projection.

10. The method according to claim 8, wherein one or more of the projections are electrically isolated from the rest of the projections and wherein current is supplied sequentially to each electrically isolated projection.

11. The method according to claim 1, wherein the anvil is an elongated member having a substantially uniform cross-section and a sharpened end, and wherein the anvil is inserted in the target vessel by puncturing the wall of the target vessel with the sharpened end of the anvil.

12. The method according to claim 1, wherein the incision in the target vessel is made with a cutting device which is electrically connected to a power source, said method further comprising the step of causing electric current to flow through the tissue between the electrode surfaces on the anvil and the cutting device while the incision is being made to cauterize the incision.

13. The method according to claim 1, wherein the anastomosis is performed on a pressurized target vessel.

14. An anastomosis system for connecting a graft vessel to a target vessel by the application of energy, the anastomosis system comprising:
   an elongated anvil having tissue contacting surfaces thereon; and
   a graft vessel fixture comprising clamping members each having one or more clamping surfaces adapted to compress the graft and target vessel tissue on opposite sides of the graft vessel against the tissue contacting surfaces of the anvil said fixture being movable relative to the anvil so as to allow the graft and target vessel tissue to be clamped between the anvil and the fixture at the anastomosis site;
   wherein the tissue contacting surfaces of the anvil or the clamping surfaces of the fixture are provided with one or more energy applying surfaces.

15. The anastomosis system according to claim 14, wherein the energy applying surfaces are electrodes provided on both the tissue contacting surfaces of the anvil and the clamping surfaces of the graft vessel fixture.

16. The anastomosis system according to claim 15, wherein the clamping surfaces of the fixture comprise a plurality of projections each of which forms a separate clamping surface with the anvil.

17. The anastomosis system according to claim 15, wherein the tissue contacting surfaces of the anvil comprise a plurality of projections each of which forms a separate clamping surface with the graft vessel fixture.

18. The anastomosis system according to claim 16, wherein one or more of the projections are electrically isolated from the other projections.

19. The anastomosis system according to claims 17, wherein one or more of the projections are electrically isolated from the other projections.

20. The anastomosis system according to claim 14, further comprising a cutting device which is electrically connected to a power source to form an electrode.

21. The anastomosis system according to claim 14, wherein the anvil comprises a plurality of optical fibers having ends which are exposed at the tissue contacting surfaces thereof.

22. The anastomosis system according to claim 14, wherein the clamping surfaces of the graft vessel fixture comprise optical fibers having ends which are exposed at tissue contacting surfaces thereof.

23. The anastomosis system according to claim 14, wherein tissue clamping surfaces of the graft vessel fixture comprise wires having ends which are exposed at tissue contacting surfaces thereof.

24. The anastomosis system according to claim 14, wherein said fixture further comprises two arms movably mounted with respect to the clamping members, said clamping members and movable arms adapted for receiving and holding portions of the graft vessel therebetween.

25. An anvil for use in performing anastomosis between a graft vessel and a target vessel by the application of energy, the anvil comprising:
   a handle; and
   an elongated anvil arm extending from the handle, the anvil arm having at least one energy applying surface on a tissue contacting surface thereof.

26. The anvil according to claim 25, wherein the energy applying surface comprises one or more electrode patches on an upper tissue contacting surface thereof.

27. The anvil according to claim 25, wherein the anvil further comprises a temperature or impedance sensor.

28. The anvil according to claim 25, wherein the energy applying surface comprises a plurality of optical fibers having ends which are exposed at the tissue contacting surface thereof.

29. The anvil according to claim 25, wherein the anvil further comprises at least one energy applying assembly movably mounted in a track such that the assembly can be moved along the length of the anvil.

30. The anvil according to claim 29, wherein the energy applying assembly comprises optical fibers for application of laser energy.

31. The anvil according to claim 29, wherein the energy applying assembly comprises wires for application of ultrasonic energy.

32. The anvil according to claim 29, wherein the energy applying assembly comprises electrodes for application of RF energy.

33. A method of performing an anastomosis between a target vessel and the end of a graft vessel comprising steps of:
   applying a tissue adhesive to mating surfaces of the graft vessel or target vessel;
   inserting an elongated anvil through the wall of the target vessel and positioning the anvil along an interior of the target vessel wall;
   positioning the end of the graft vessel adjacent an exterior of the target vessel wall; and
   curing the adhesive.

34. The method of claim 33, further comprising steps of:
   making an opening in the target vessel to allow blood to flow between the target vessel and the graft vessel; and
   removing the anvil.

35. The method of claim 33, wherein the adhesive is activated by heat or light energy, the method further comprising applying heat or light energy to the adhesive.

36. The method of claim 33, wherein the tissue adhesive is applied to the mating surfaces before the graft vessel is positioned adjacent the target vessel wall.

37. The method of claim 33, wherein the tissue adhesive is applied to the mating surfaces after the graft vessel is positioned adjacent the target vessel wall.

38. The method of claim 37, wherein the tissue adhesive is applied to the mating surfaces with one or more hollow tubes or needles.

39. The method of claim 38, wherein the tissue adhesive is applied to the mating surfaces by injecting the adhesive through an opening in the graft vessel tissue.

40. An anastomosis system for connecting a graft vessel to a target vessel using a tissue adhesive, the anastomosis system comprising:

an elongated anvil having tissue contacting surfaces thereon; and a graft vessel fixture comprising clamping members each having one or more clamping surfaces adapted to compress the graft and target vessel tissue on opposite sides of the graft vessel against the tissue contacting surfaces of the anvil, said fixture being movable relative to the anvil so as to allow the graft and target vessel tissue to be clamped between the anvil and the fixture at the anastomosis site;

wherein the anvil or the graft vessel fixture is provided with one or more tissue adhesive applicators adapted to supply a tissue adhesive to mating surfaces of the graft or target vessel.

41. The anastomosis system of claim 40, wherein the anvil is provided with a tissue adhesive applicator.

42. The anastomosis system of claim 40, wherein the graft vessel fixture further comprises a pin assembly adapted to trap the graft vessel against the clamping members, wherein the pin assembly is provided with one or more tissue adhesive applicators.

43. The anastomosis system of claim 40, wherein the tissue adhesive applicator is a hollow tube or needle.

* * * * *